(12) United States Patent
Gill

(10) Patent No.: US 9,730,778 B2
(45) Date of Patent: *Aug. 15, 2017

(54) CURING LIGHT DEVICE

(71) Applicant: Kerr Corporation, Orange, CA (US)

(72) Inventor: Owen Gill, Southbury, CT (US)

(73) Assignee: Kerr Corporation, Orange, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/754,123

(22) Filed: Jun. 29, 2015

(65) Prior Publication Data

US 2015/0297328 A1 Oct. 22, 2015

Related U.S. Application Data

(63) Continuation of application No. 12/752,335, filed on Apr. 1, 2010, now Pat. No. 9,066,777.

(Continued)

(51) Int. Cl.
*A61C 13/15* (2006.01)
*F21V 29/70* (2015.01)
(Continued)

(52) U.S. Cl.
CPC .............. *A61C 19/004* (2013.01); *F21L 4/02* (2013.01); *F21L 4/08* (2013.01); *F21V 5/048* (2013.01);
(Continued)

(58) Field of Classification Search
CPC ....... A61C 19/004; F21V 29/70; F21V 5/048; F21V 19/02; F21V 23/003; F21V 23/02;
(Continued)

(56) References Cited

U.S. PATENT DOCUMENTS

| 687,738 A | 12/1901 | Fleming |
| 2,218,678 A | 10/1940 | Hoffman |

(Continued)

FOREIGN PATENT DOCUMENTS

| CA | 2190225 A1 | 6/1997 |
| CA | 2266845 A1 | 10/1999 |

(Continued)

OTHER PUBLICATIONS

Burgess, John O. et al., An Evaluation of Four Light-Curing Units Comparing Soft and Hard Curing, ; Pract. Periodont Aesthet. Dent. 11(1), 125-132, 1999.

(Continued)

*Primary Examiner* — Mary Ellen Bowman
(74) *Attorney, Agent, or Firm* — Wood Herron & Evans LLP

(57) ABSTRACT

A curing light device for curing a compound includes a housing and a tip structure configured to be removably coupled with the housing. A light emitting device operable for emitting light in a wavelength range suitable for curing a light curable compound is positioned at the distal end of the tip structure. Electrical components are positioned at the proximal end of the tip structure and coupled with the at least one light emitting device and are configured for engaging complementary electrical components positioned in the housing for providing power to the light emitting device. A portion of the tip structure extends beyond the proximal end of the tip structure and is configured to be received by a feature in the housing for physically aligning the tip structure in the housing and for aligning the electrical components. A power supply circuit is rechargeable and includes an ultracapacitor element.

20 Claims, 12 Drawing Sheets

Related U.S. Application Data

(60) Provisional application No. 61/166,130, filed on Apr. 2, 2009.

(51) Int. Cl.

| | | |
|---|---|---|
| *F21L 4/02* | (2006.01) | |
| *F21L 4/08* | (2006.01) | |
| *F21V 5/04* | (2006.01) | |
| *F21V 19/02* | (2006.01) | |
| *F21V 23/00* | (2015.01) | |
| *F21V 23/02* | (2006.01) | |
| *F21V 23/06* | (2006.01) | |
| *F21V 33/00* | (2006.01) | |
| F21W 131/202 | (2006.01) | |
| F21Y 115/10 | (2016.01) | |

(52) U.S. Cl.
CPC ............ *F21V 19/02* (2013.01); *F21V 23/003* (2013.01); *F21V 23/02* (2013.01); *F21V 23/06* (2013.01); *F21V 29/70* (2015.01); *F21V 33/0068* (2013.01); *F21W 2131/202* (2013.01); *F21Y 2115/10* (2016.08)

(58) Field of Classification Search
CPC ........ F21V 23/06; F21V 33/0068; F21L 4/02; F21L 4/08
See application file for complete search history.

(56) References Cited

U.S. PATENT DOCUMENTS

| | | |
|---|---|---|
| 3,310,358 A | 3/1967 | Marcatili et al. |
| 3,605,039 A | 9/1971 | Harris et al. |
| 3,638,013 A | 1/1972 | Keller |
| 3,655,483 A | 4/1972 | Borrel et al. |
| 3,666,180 A | 5/1972 | Coombs et al. |
| 3,666,645 A | 5/1972 | Ransohoff |
| 3,704,928 A | 12/1972 | Coombs et al. |
| 3,712,984 A | 1/1973 | Lienhard |
| 3,733,481 A | 5/1973 | Kuyt |
| 3,755,900 A | 9/1973 | Friedman |
| 3,763,442 A | 10/1973 | McMahan |
| 3,787,678 A | 1/1974 | Rainer |
| 3,801,202 A | 4/1974 | Breaux |
| 3,829,676 A | 8/1974 | Nelson et al. |
| 3,850,675 A | 11/1974 | Miller |
| 3,868,513 A | 2/1975 | Gonser |
| 3,930,149 A | 12/1975 | French |
| 3,931,589 A | 1/1976 | Aisenberg et al. |
| 3,943,046 A | 3/1976 | De Sorga et al. |
| 3,962,656 A | 6/1976 | Peressini |
| 3,962,657 A | 6/1976 | Redman et al. |
| 3,967,214 A | 6/1976 | Thatcher |
| 3,970,856 A | 7/1976 | Mahaffey et al. |
| 3,970,962 A | 7/1976 | Peressini et al. |
| 4,007,430 A | 2/1977 | Fletcher et al. |
| 4,032,773 A | 6/1977 | Halliday, Jr. et al. |
| 4,041,304 A | 8/1977 | Spector |
| 4,045,663 A | 8/1977 | Young |
| RE29,421 E | 9/1977 | Scott |
| 4,048,490 A | 9/1977 | Troue |
| 4,053,845 A | 10/1977 | Gould |
| 4,061,986 A | 12/1977 | Barker |
| 4,080,737 A | 3/1978 | Fleer |
| 4,092,580 A | 5/1978 | Prinsze |
| 4,112,335 A | 9/1978 | Gonser |
| 4,114,274 A | 9/1978 | Jones |
| 4,114,946 A | 9/1978 | Hoffmeister et al. |
| 4,149,086 A | 4/1979 | Nath |
| 4,151,583 A | 4/1979 | Miller |
| 4,161,436 A | 7/1979 | Gould |
| 4,165,265 A | 8/1979 | Nakabayashi et al. |
| 4,178,221 A | 12/1979 | Boutin et al. |
| 4,182,665 A | 1/1980 | Mibu et al. |
| 4,184,196 A | 1/1980 | Moret et al. |
| 4,185,891 A | 1/1980 | Kaestner |
| 4,186,748 A | 2/1980 | Schlager |
| 4,191,622 A | 3/1980 | Phillips et al. |
| 4,203,080 A | 5/1980 | Wright et al. |
| 4,209,907 A | 7/1980 | Tsukada et al. |
| 4,221,994 A | 9/1980 | Friedman et al. |
| 4,224,525 A | 9/1980 | Phillips et al. |
| 4,229,658 A | 10/1980 | Gonser |
| 4,230,453 A | 10/1980 | Reimers |
| 4,230,766 A | 10/1980 | Gaussens et al. |
| 4,233,649 A | 11/1980 | Scheer et al. |
| 4,245,890 A | 1/1981 | Hartman et al. |
| 4,266,535 A | 5/1981 | Moret |
| 4,280,273 A | 7/1981 | Vincent |
| 4,281,366 A | 7/1981 | Wurster et al. |
| 4,298,005 A | 11/1981 | Mutzhas |
| 4,298,806 A | 11/1981 | Herold |
| 4,308,120 A | 12/1981 | Pennewiss et al. |
| 4,309,617 A | 1/1982 | Long |
| 4,313,969 A | 2/1982 | Matthews et al. |
| 4,325,107 A | 4/1982 | MacLeod |
| 4,329,421 A | 5/1982 | Wisnosky et al. |
| 4,337,759 A | 7/1982 | Popovich et al. |
| 4,348,180 A | 9/1982 | Schuss |
| 4,351,853 A | 9/1982 | Jochum et al. |
| 4,357,648 A | 11/1982 | Nelson |
| 4,360,860 A | 11/1982 | Johnson et al. |
| 4,385,344 A | 5/1983 | Gonser |
| RE31,279 E | 6/1983 | Mefferd et al. |
| 4,391,588 A | 7/1983 | Matsui |
| 4,392,827 A | 7/1983 | Martin |
| 4,398,885 A | 8/1983 | Loge et al. |
| 4,402,524 A | 9/1983 | D'Antonio et al. |
| 4,411,931 A | 10/1983 | Duong |
| 4,412,134 A | 10/1983 | Herold et al. |
| 4,421,784 A | 12/1983 | Troue |
| 4,445,858 A | 5/1984 | Johnson |
| 4,447,151 A | 5/1984 | McLellan et al. |
| 4,450,139 A | 5/1984 | Bussiere et al. |
| 4,477,901 A | 10/1984 | Braband et al. |
| 4,479,225 A | 10/1984 | Mohler et al. |
| 4,504,231 A | 3/1985 | Koblitz et al. |
| 4,522,593 A | 6/1985 | Fischer |
| 4,522,594 A | 6/1985 | Stark et al. |
| 4,544,467 A | 10/1985 | Bunker et al. |
| 4,551,100 A | 11/1985 | Fischer |
| 4,571,377 A | 2/1986 | McGinniss et al. |
| 4,573,159 A | 2/1986 | Aagano et al. |
| 4,578,055 A | 3/1986 | Fischer |
| 4,582,701 A | 4/1986 | Piechota, Jr. |
| 4,610,630 A | 9/1986 | Betush |
| 4,611,327 A | 9/1986 | Clark et al. |
| 4,611,992 A | 9/1986 | Lokken |
| 4,613,972 A | 9/1986 | Bettman |
| 4,615,033 A | 9/1986 | Nakano et al. |
| 4,615,034 A | 9/1986 | von Gunten et al. |
| 4,625,317 A | 11/1986 | Kolb et al. |
| 4,634,953 A | 1/1987 | Shoji et al. |
| 4,635,272 A | 1/1987 | Kamide et al. |
| 4,656,635 A | 4/1987 | Baer et al. |
| 4,661,070 A | 4/1987 | Friedman |
| 4,665,524 A | 5/1987 | Cotter |
| 4,666,405 A | 5/1987 | Ericson |
| 4,666,406 A | 5/1987 | Kanca, III |
| 4,673,353 A | 6/1987 | Nevin |
| 4,674,092 A | 6/1987 | Cannon |
| 4,682,950 A | 7/1987 | Dragan |
| 4,687,663 A | 8/1987 | Schaeffer |
| 4,696,010 A | 9/1987 | Eastman |
| 4,697,269 A | 9/1987 | Ohara |
| 4,698,730 A | 10/1987 | Sakai et al. |
| 4,698,835 A | 10/1987 | Ono et al. |
| 4,704,583 A | 11/1987 | Gould |
| 4,713,825 A | 12/1987 | Adsett |
| 4,716,296 A | 12/1987 | Bussiere et al. |
| 4,716,569 A | 12/1987 | Bees |
| 4,717,605 A | 1/1988 | Urban et al. |
| 4,723,257 A | 2/1988 | Baer et al. |

(56) References Cited

U.S. PATENT DOCUMENTS

| | | |
|---|---|---|
| 4,725,231 A | 2/1988 | Boinot et al. |
| 4,727,554 A | 2/1988 | Watanabe |
| 4,729,076 A | 3/1988 | Masami et al. |
| 4,733,937 A | 3/1988 | Lia et al. |
| 4,746,685 A | 5/1988 | Masuhara et al. |
| 4,757,381 A | 7/1988 | Cooper et al. |
| 4,762,862 A | 8/1988 | Yada et al. |
| 4,762,962 A | 8/1988 | Wideman |
| 4,769,824 A | 9/1988 | Seki |
| 4,784,135 A | 11/1988 | Blum et al. |
| 4,792,692 A | 12/1988 | Herold et al. |
| 4,794,315 A | 12/1988 | Pederson et al. |
| 4,810,194 A | 3/1989 | Snedden |
| 4,817,096 A | 3/1989 | Nighan et al. |
| 4,819,139 A | 4/1989 | Thomas |
| 4,826,431 A | 5/1989 | Fujimura et al. |
| 4,835,344 A | 5/1989 | Iyogi et al. |
| 4,836,782 A | 6/1989 | Gonser |
| 4,839,566 A | 6/1989 | Herold et al. |
| 4,843,110 A | 6/1989 | Kubota et al. |
| 4,846,546 A | 7/1989 | Cuda |
| 4,849,320 A | 7/1989 | Irving et al. |
| 4,857,801 A | 8/1989 | Farrell |
| 4,862,469 A | 8/1989 | Couillaud et al. |
| 4,872,936 A | 10/1989 | Engelbrecht |
| 4,877,401 A | 10/1989 | Higuchi et al. |
| 4,887,271 A | 12/1989 | Taylor |
| 4,888,489 A | 12/1989 | Bryan |
| 4,895,517 A | 1/1990 | Fischer |
| 4,896,330 A | 1/1990 | Krueger et al. |
| 4,904,872 A | 2/1990 | Grix et al. |
| 4,923,905 A | 5/1990 | Masuhara et al. |
| 4,933,380 A | 6/1990 | Aihara et al. |
| 4,933,381 A | 6/1990 | Hager |
| 4,935,665 A | 6/1990 | Murata |
| 4,936,776 A | 6/1990 | Kwiatkowski |
| 4,936,808 A | 6/1990 | Lee |
| 4,941,873 A | 7/1990 | Fischer |
| 4,948,215 A | 8/1990 | Friedman |
| 4,963,798 A | 10/1990 | McDermott |
| 4,968,251 A | 11/1990 | Darnell |
| 4,971,556 A | 11/1990 | Ritano et al. |
| 4,983,380 A | 1/1991 | Yarborough |
| 4,983,381 A | 1/1991 | Torres Zaragoza |
| 4,989,217 A | 1/1991 | Ostler |
| 4,990,089 A | 2/1991 | Munro |
| 4,992,045 A | 2/1991 | Beisel |
| 4,995,540 A | 2/1991 | Colin et al. |
| 4,999,310 A | 3/1991 | Kim |
| 5,002,854 A | 3/1991 | Fan et al. |
| 5,002,855 A | 3/1991 | Fan et al. |
| 5,003,434 A | 3/1991 | Gonser et al. |
| 5,005,181 A | 4/1991 | Yoshioka et al. |
| 5,007,737 A | 4/1991 | Hirleman, Jr. |
| 5,007,837 A | 4/1991 | Werly |
| 5,009,885 A | 4/1991 | Yarborough |
| 5,013,144 A | 5/1991 | Silverglate et al. |
| 5,013,240 A | 5/1991 | Bailey et al. |
| 5,017,140 A | 5/1991 | Ascher |
| 5,029,957 A | 7/1991 | Hood |
| 5,031,768 A | 7/1991 | Fischer |
| 5,032,178 A | 7/1991 | Cornell |
| 5,033,650 A | 7/1991 | Colin et al. |
| 5,040,182 A | 8/1991 | Spinelli et al. |
| 5,041,280 A | 8/1991 | Smigel |
| 5,043,361 A | 8/1991 | Kubota et al. |
| 5,043,634 A | 8/1991 | Rothwell, Jr. et al. |
| 5,046,810 A | 9/1991 | Steiner et al. |
| 5,055,743 A | 10/1991 | Ekstrand |
| 5,063,255 A | 11/1991 | Hasegawa et al. |
| 5,070,258 A | 12/1991 | Izumi et al. |
| 5,071,222 A | 12/1991 | Laakmann et al. |
| 5,092,022 A | 3/1992 | Duret et al. |
| 5,093,385 A | 3/1992 | Ali |
| 5,098,299 A | 3/1992 | Fischer |
| 5,098,303 A | 3/1992 | Fischer |
| 5,105,347 A | 4/1992 | Ruud et al. |
| 5,115,761 A | 5/1992 | Hood |
| 5,123,845 A | 6/1992 | Vassiliadis et al. |
| 5,127,730 A | 7/1992 | Brelje et al. |
| 5,137,448 A | 8/1992 | Dougherty et al. |
| 5,139,495 A | 8/1992 | Daikuzono |
| 5,147,204 A | 9/1992 | Patten et al. |
| 5,149,659 A | 9/1992 | Hakuta et al. |
| 5,150,016 A | 9/1992 | Sawase et al. |
| 5,151,520 A | 9/1992 | Gottschalk et al. |
| 5,154,861 A | 10/1992 | McBrierty et al. |
| 5,161,879 A | 11/1992 | McDermott |
| 5,162,696 A | 11/1992 | Goodrich |
| 5,173,810 A | 12/1992 | Yamakawa |
| 5,175,077 A | 12/1992 | Grossa |
| 5,181,214 A | 1/1993 | Berger et al. |
| 5,181,215 A | 1/1993 | Sam et al. |
| RE34,196 E | 3/1993 | Munro |
| 5,189,751 A | 3/1993 | Giuliani et al. |
| 5,198,678 A | 3/1993 | Oppawsky |
| 5,201,655 A | 4/1993 | Friedman |
| 5,209,169 A | 5/1993 | Basic, Sr. |
| 5,214,658 A | 5/1993 | Ostler |
| 5,217,654 A | 6/1993 | Buckley |
| 5,224,773 A | 7/1993 | Arimura |
| 5,233,283 A | 8/1993 | Kennedy |
| 5,238,744 A | 8/1993 | Williams et al. |
| 5,240,415 A | 8/1993 | Haynie |
| 5,242,602 A | 9/1993 | Richardson et al. |
| 5,246,371 A | 9/1993 | Fischer |
| 5,254,114 A | 10/1993 | Reed, Jr. et al. |
| 5,265,792 A | 11/1993 | Harrah et al. |
| 5,269,684 A | 12/1993 | Fischer |
| 5,275,564 A | 1/1994 | Vassiliadis et al. |
| 5,278,629 A | 1/1994 | Schlager et al. |
| 5,280,536 A | 1/1994 | Dumond et al. |
| 5,283,425 A | 2/1994 | Imamura |
| 5,285,318 A | 2/1994 | Gleckman |
| 5,286,257 A | 2/1994 | Fischer |
| 5,288,231 A | 2/1994 | Kuehn et al. |
| 5,289,919 A | 3/1994 | Fischer |
| 5,290,169 A | 3/1994 | Friedman et al. |
| 5,290,259 A | 3/1994 | Fischer |
| 5,298,532 A | 3/1994 | Ali |
| 5,300,331 A | 4/1994 | Schaeffer |
| 5,302,124 A | 4/1994 | Lansing et al. |
| 5,306,143 A | 4/1994 | Levy |
| 5,312,249 A | 5/1994 | Kennedy |
| 5,316,473 A | 5/1994 | Hare |
| 5,318,562 A | 6/1994 | Levy et al. |
| 5,318,999 A | 6/1994 | Mitra et al. |
| 5,321,715 A | 6/1994 | Trost |
| 5,324,200 A | 6/1994 | Vassiliadis et al. |
| 5,328,368 A | 7/1994 | Lansing et al. |
| 5,328,462 A | 7/1994 | Fischer |
| 5,332,092 A | 7/1994 | Fischer |
| 5,346,489 A | 9/1994 | Levy et al. |
| 5,348,552 A | 9/1994 | Nakajima et al. |
| 5,349,591 A | 9/1994 | Weston et al. |
| 5,350,834 A | 9/1994 | Bobsein et al. |
| 5,356,291 A | 10/1994 | Darnell |
| 5,360,834 A | 11/1994 | Popall et al. |
| 5,364,267 A | 11/1994 | Fischer |
| 5,371,826 A | 12/1994 | Friedman |
| 5,373,114 A | 12/1994 | Kondo et al. |
| 5,376,006 A | 12/1994 | Fischer |
| 5,382,799 A | 1/1995 | May |
| 5,387,103 A | 2/1995 | Fischer |
| 5,388,988 A | 2/1995 | Goisser et al. |
| 5,395,490 A | 3/1995 | Hoff et al. |
| 5,397,892 A | 3/1995 | Abdelqader |
| 5,409,631 A | 4/1995 | Fischer |
| 5,415,543 A | 5/1995 | Rozmajzl, Jr. |
| 5,418,384 A | 5/1995 | Yamana et al. |
| 5,420,758 A | 5/1995 | Liang |
| 5,420,768 A | 5/1995 | Kennedy |
| 5,425,641 A | 6/1995 | Fischer |
| 5,425,953 A | 6/1995 | Sintov et al. |

(56)  References Cited

U.S. PATENT DOCUMENTS

| | | |
|---|---|---|
| 5,444,104 A | 8/1995 | Waknine |
| 5,445,523 A | 8/1995 | Fischer et al. |
| 5,448,323 A | 9/1995 | Clark et al. |
| 5,449,703 A | 9/1995 | Mitra et al. |
| 5,457,611 A | 10/1995 | Verderber |
| 5,464,348 A | 11/1995 | Fischer et al. |
| 5,467,362 A | 11/1995 | Murray |
| 5,471,129 A | 11/1995 | Mann |
| 5,472,991 A | 12/1995 | Schmitt et al. |
| 5,475,417 A | 12/1995 | Ogata et al. |
| 5,478,235 A | 12/1995 | Schuldt et al. |
| 5,485,317 A | 1/1996 | Perissinotto et al. |
| 5,487,662 A | 1/1996 | Kipke et al. |
| 5,501,579 A | 3/1996 | Kimura et al. |
| 5,501,599 A | 3/1996 | Rechmann |
| 5,521,227 A | 5/1996 | Palazzotto et al. |
| 5,521,392 A | 5/1996 | Kennedy et al. |
| 5,527,261 A | 6/1996 | Monroe et al. |
| 5,530,632 A | 6/1996 | Shikano et al. |
| 5,530,633 A | 6/1996 | Yuen |
| 5,534,559 A | 7/1996 | Leppard et al. |
| 5,534,562 A | 7/1996 | Jensen et al. |
| 5,535,230 A | 7/1996 | Abe |
| 5,536,758 A | 7/1996 | Boldt |
| 5,550,853 A | 8/1996 | Ostler |
| 5,558,230 A | 9/1996 | Fischer et al. |
| 5,575,655 A | 11/1996 | Darnell |
| 5,598,005 A | 1/1997 | Wang et al. |
| 5,603,701 A | 2/1997 | Fischer |
| 5,608,290 A | 3/1997 | Hutchisson et al. |
| 5,611,687 A | 3/1997 | Wagner |
| 5,613,751 A | 3/1997 | Parker et al. |
| 5,616,141 A | 4/1997 | Cipolla |
| 5,617,492 A | 4/1997 | Beach et al. |
| 5,618,273 A | 4/1997 | Fischer |
| 5,621,303 A | 4/1997 | Shalvi |
| 5,632,739 A | 5/1997 | Anderson et al. |
| 5,634,711 A | 6/1997 | Kennedy et al. |
| 5,635,162 A | 6/1997 | Fischer |
| 5,639,158 A | 6/1997 | Sato |
| 5,642,933 A | 7/1997 | Hitora |
| 5,643,206 A | 7/1997 | Fischer |
| 5,645,428 A | 7/1997 | Yarborough |
| 5,660,461 A | 8/1997 | Ignatius et al. |
| 5,664,042 A | 9/1997 | Kennedy |
| 5,665,066 A | 9/1997 | Fischer |
| 5,667,386 A | 9/1997 | Black et al. |
| 5,669,769 A | 9/1997 | Disel |
| 5,678,998 A | 10/1997 | Honkura et al. |
| 5,685,712 A | 11/1997 | Fischer |
| 5,688,042 A | 11/1997 | Madadi et al. |
| 5,689,866 A | 11/1997 | Kasai et al. |
| 5,692,900 A | 12/1997 | Fischer |
| 5,697,903 A | 12/1997 | Fischer |
| 5,697,918 A | 12/1997 | Fischer et al. |
| 5,698,866 A | 12/1997 | Doiron et al. |
| 5,700,148 A | 12/1997 | Fischer et al. |
| 5,702,250 A | 12/1997 | Kipke |
| 5,707,139 A | 1/1998 | Haitz |
| 5,708,052 A | 1/1998 | Fischer et al. |
| 5,711,665 A | 1/1998 | Adam et al. |
| 5,713,738 A | 2/1998 | Yarborough |
| 5,722,829 A | 3/1998 | Wilcox et al. |
| 5,722,833 A | 3/1998 | Fischer et al. |
| 5,725,843 A | 3/1998 | Fischer |
| 5,733,029 A | 3/1998 | Monroe |
| 5,741,132 A | 4/1998 | Usui et al. |
| 5,746,598 A | 5/1998 | Fischer |
| 5,747,363 A | 5/1998 | Wei et al. |
| 5,749,724 A | 5/1998 | Cheng |
| 5,759,032 A | 6/1998 | Bartel |
| 5,762,605 A | 6/1998 | Cane et al. |
| 5,766,011 A | 6/1998 | Sibner |
| 5,766,012 A | 6/1998 | Rosenbaum et al. |
| 5,768,458 A | 6/1998 | Ro et al. |
| 5,770,105 A | 6/1998 | Fischer |
| 5,770,182 A | 6/1998 | Fischer |
| 5,772,643 A | 6/1998 | Howell et al. |
| 5,775,904 A | 7/1998 | Riitano |
| 5,776,127 A | 7/1998 | Anderson et al. |
| 5,782,552 A | 7/1998 | Green et al. |
| 5,782,553 A | 7/1998 | McDermott |
| 5,785,955 A | 7/1998 | Fischer |
| 5,790,794 A | 8/1998 | DuLac et al. |
| 5,791,898 A | 8/1998 | Maissami |
| 5,797,740 A | 8/1998 | Lundvik |
| 5,800,163 A | 9/1998 | Rueggeberg et al. |
| 5,803,579 A | 9/1998 | Turnbull et al. |
| 5,803,729 A | 9/1998 | Tsimerman |
| 5,803,734 A | 9/1998 | Knutson |
| 5,807,397 A | 9/1998 | Barreras |
| 5,816,804 A | 10/1998 | Fischer |
| 5,838,247 A | 11/1998 | Bladowski |
| 5,846,058 A | 12/1998 | Fischer |
| 5,847,020 A | 12/1998 | Ibsen et al. |
| 5,851,512 A | 12/1998 | Fischer |
| 5,855,870 A | 1/1999 | Fischer |
| 5,856,373 A | 1/1999 | Kaisaki et al. |
| 5,857,767 A | 1/1999 | Hochstein |
| 5,858,332 A | 1/1999 | Jensen et al. |
| 5,860,806 A | 1/1999 | Pranitis, Jr. et al. |
| 5,865,529 A | 2/1999 | Yan |
| 5,865,623 A | 2/1999 | Suh |
| 5,868,769 A | 2/1999 | Rosenblood et al. |
| 5,880,839 A | 3/1999 | Ishizuka et al. |
| 5,882,082 A | 3/1999 | Moore |
| 5,882,201 A | 3/1999 | Salem |
| 5,885,082 A | 3/1999 | Levy |
| 5,886,401 A | 3/1999 | Liu |
| 5,890,900 A | 4/1999 | Fischer et al. |
| 5,890,901 A | 4/1999 | Fischer et al. |
| 5,897,314 A | 4/1999 | Hack et al. |
| 5,905,268 A | 5/1999 | Garcia et al. |
| 5,908,294 A | 6/1999 | Schick et al. |
| 5,908,295 A | 6/1999 | Kawata |
| 5,912,470 A | 6/1999 | Eibofner et al. |
| 5,921,652 A | 7/1999 | Parker et al. |
| 5,921,777 A | 7/1999 | Dorman |
| 5,922,307 A | 7/1999 | Montgomery |
| 5,925,715 A | 7/1999 | Mitra |
| 5,928,220 A | 7/1999 | Shimoji |
| 5,928,505 A | 7/1999 | Inakagata et al. |
| 5,929,788 A | 7/1999 | Vukosic |
| 5,931,676 A | 8/1999 | Honkura et al. |
| 5,936,353 A | 8/1999 | Triner et al. |
| 5,947,278 A | 9/1999 | Sawhney et al. |
| 5,967,778 A | 10/1999 | Riitano |
| 5,971,755 A | 10/1999 | Liebermann et al. |
| 5,975,714 A | 11/1999 | Vetorino et al. |
| 5,975,895 A | 11/1999 | Sullivan |
| 5,980,295 A | 11/1999 | Lai et al. |
| 5,985,249 A | 11/1999 | Fischer |
| 5,990,900 A | 11/1999 | Seago |
| 6,001,058 A | 12/1999 | Sano et al. |
| 6,008,264 A | 12/1999 | Ostler et al. |
| 6,019,482 A | 2/2000 | Everett |
| 6,019,493 A | 2/2000 | Kuo et al. |
| 6,019,599 A | 2/2000 | Volcker et al. |
| 6,028,694 A | 2/2000 | Schmidt |
| 6,028,788 A | 2/2000 | Choi et al. |
| 6,033,087 A | 3/2000 | Shozo et al. |
| 6,033,223 A | 3/2000 | Narusawa et al. |
| 6,036,336 A | 3/2000 | Wu |
| 6,045,240 A | 4/2000 | Hochstein |
| 6,046,460 A | 4/2000 | Mertins |
| 6,059,421 A | 5/2000 | White et al. |
| 6,065,965 A | 5/2000 | Rechmann |
| 6,068,474 A | 5/2000 | Senn et al. |
| 6,072,576 A | 6/2000 | McDonald et al. |
| 6,077,073 A | 6/2000 | Jacob |
| 6,079,861 A | 6/2000 | Woodward et al. |
| 6,086,366 A | 7/2000 | Mueller et al. |
| 6,086,367 A | 7/2000 | Levy |
| 6,089,740 A | 7/2000 | Forehand et al. |

(56) References Cited

U.S. PATENT DOCUMENTS

| | | |
|---|---|---|
| 6,095,661 A | 8/2000 | Lebens et al. |
| 6,095,812 A | 8/2000 | Senn et al. |
| 6,099,520 A | 8/2000 | Shimoji |
| 6,102,696 A | 8/2000 | Osterwalder et al. |
| 6,103,203 A | 8/2000 | Fischer |
| 6,123,545 A | 9/2000 | Eggler et al. |
| 6,132,213 A | 10/2000 | Knorpp et al. |
| 6,155,823 A | 12/2000 | Nagel |
| 6,157,661 A | 12/2000 | Walker et al. |
| 6,159,005 A | 12/2000 | Herold et al. |
| 6,161,937 A | 12/2000 | Rosenstatter |
| 6,168,431 B1 | 1/2001 | Narusawa et al. |
| 6,171,105 B1 | 1/2001 | Sarmadi |
| 6,186,786 B1 | 2/2001 | Trushkowsky |
| 6,190,020 B1 | 2/2001 | Hartley |
| 6,193,510 B1 | 2/2001 | Tsimerman |
| 6,200,134 B1 | 3/2001 | Kovac et al. |
| 6,203,325 B1 | 3/2001 | Honkura et al. |
| 6,208,788 B1 | 3/2001 | Nosov |
| 6,210,042 B1 | 4/2001 | Wang et al. |
| 6,220,722 B1 | 4/2001 | Begemann |
| 6,254,388 B1 | 7/2001 | Yarborough |
| 6,257,883 B1 | 7/2001 | Voudouris |
| 6,266,576 B1 | 7/2001 | Okada et al. |
| 6,270,343 B1 | 8/2001 | Martin |
| 6,280,187 B1 | 8/2001 | Slone |
| 6,280,188 B1 | 8/2001 | Ross |
| 6,282,013 B1 | 8/2001 | Ostler et al. |
| 6,299,450 B1 | 10/2001 | Honkura et al. |
| 6,318,996 B1 | 11/2001 | Melikechi et al. |
| 6,322,358 B1 | 11/2001 | Senn et al. |
| 6,325,623 B1 | 12/2001 | Melnyk et al. |
| 6,328,456 B1 | 12/2001 | Mize |
| 6,331,111 B1 | 12/2001 | Cao |
| 6,345,982 B1 | 2/2002 | Meyer |
| 6,361,192 B1 | 3/2002 | Fussell et al. |
| 6,361,489 B1 | 3/2002 | Tsai |
| 6,364,506 B1 | 4/2002 | Gallo |
| 6,371,826 B1 | 4/2002 | Pestonji |
| 6,379,149 B1 | 4/2002 | Franetzki |
| 6,382,967 B1 | 5/2002 | Rohner et al. |
| 6,384,099 B1 | 5/2002 | Ostler et al. |
| 6,398,398 B1 | 6/2002 | Moschkowitz |
| 6,402,511 B1 | 6/2002 | Calderwood |
| 6,417,917 B1 | 7/2002 | Jung et al. |
| 6,419,483 B1 | 7/2002 | Adam et al. |
| 6,425,761 B1 | 7/2002 | Eibofner |
| 6,439,888 B1 | 8/2002 | Boutoussov et al. |
| 6,444,725 B1 | 9/2002 | Trom et al. |
| 6,454,789 B1 | 9/2002 | Chen et al. |
| 6,465,961 B1 | 10/2002 | Cao |
| 6,468,077 B1 | 10/2002 | Melikechi et al. |
| 6,478,447 B2 | 11/2002 | Yen |
| 6,482,004 B1 | 11/2002 | Senn et al. |
| 6,485,301 B1 | 11/2002 | Gemunder et al. |
| 6,498,108 B2 | 12/2002 | Cao et al. |
| 6,511,317 B2 | 1/2003 | Melikechi et al. |
| 6,511,321 B1 | 1/2003 | Trushkowsky et al. |
| 6,514,075 B1 | 2/2003 | Jacob |
| 6,522,086 B2 | 2/2003 | Gemunder et al. |
| 6,528,555 B1 | 3/2003 | Nikutowski et al. |
| 6,554,463 B2 | 4/2003 | Hooker et al. |
| 6,558,048 B2 | 5/2003 | Kuhara et al. |
| 6,558,829 B1 | 5/2003 | Faris et al. |
| 6,561,802 B2 | 5/2003 | Alexander |
| 6,561,806 B2 | 5/2003 | Kyotani et al. |
| 6,563,269 B2 | 5/2003 | Robinett et al. |
| 6,602,074 B1 | 8/2003 | Suh et al. |
| 6,604,847 B2 | 8/2003 | Lehrer |
| 6,611,110 B1 | 8/2003 | Fregoso |
| 6,634,770 B2 | 10/2003 | Cao |
| 6,634,771 B2 | 10/2003 | Cao |
| 6,635,363 B1 | 10/2003 | Duclos et al. |
| 6,638,063 B2 | 10/2003 | Otsuka |
| 6,666,612 B2 | 12/2003 | Lorigny et al. |
| 6,692,250 B1 | 2/2004 | Decaudin et al. |
| 6,692,251 B1 | 2/2004 | Logan et al. |
| 6,692,252 B2 | 2/2004 | Scott |
| 6,692,525 B2 | 2/2004 | Brady et al. |
| 6,695,614 B2 | 2/2004 | Plank |
| 6,700,158 B1 | 3/2004 | Cao et al. |
| 6,702,576 B2 | 3/2004 | Fischer et al. |
| 6,709,128 B2 | 3/2004 | Gordon et al. |
| 6,709,270 B2 | 3/2004 | Honkura et al. |
| 6,719,446 B2 | 4/2004 | Cao |
| 6,719,558 B2 | 4/2004 | Cao |
| 6,719,559 B2 | 4/2004 | Cao |
| 6,746,885 B2 | 6/2004 | Cao |
| 6,755,647 B2 | 6/2004 | Melikechi et al. |
| 6,755,648 B2 | 6/2004 | Cao |
| 6,755,649 B2 | 6/2004 | Cao |
| 6,764,719 B2 | 7/2004 | Russell et al. |
| 6,767,109 B2 | 7/2004 | Plank et al. |
| 6,780,010 B2 | 8/2004 | Cao |
| 6,783,362 B2 | 8/2004 | Cao |
| 6,783,810 B2 | 8/2004 | Jin et al. |
| 6,793,490 B2 | 9/2004 | Bianchetti et al. |
| 6,799,967 B2 | 10/2004 | Cao |
| 6,815,241 B2 | 11/2004 | Wang |
| 6,821,119 B2 | 11/2004 | Shortt et al. |
| 6,824,294 B2 | 11/2004 | Cao |
| 6,829,260 B2 | 12/2004 | Hsia et al. |
| 6,832,849 B2 | 12/2004 | Yoneda et al. |
| 6,835,219 B2 | 12/2004 | Gittleman |
| 6,857,873 B2 | 2/2005 | Bianchetti et al. |
| 6,873,111 B2 | 3/2005 | Ito et al. |
| 6,880,954 B2 | 4/2005 | Ollett et al. |
| 6,880,985 B2 | 4/2005 | Hoshino et al. |
| 6,890,175 B2 | 5/2005 | Fischer et al. |
| 6,890,234 B2 | 5/2005 | Bortscheller et al. |
| 6,910,886 B2 | 6/2005 | Cao |
| 6,918,762 B2 | 7/2005 | Gill et al. |
| 6,926,524 B2 | 8/2005 | Cao |
| 6,929,472 B2 | 8/2005 | Cao |
| 6,932,600 B2 | 8/2005 | Cao |
| 6,933,702 B2 | 8/2005 | Hsu |
| 6,940,659 B2 | 9/2005 | McLean et al. |
| 6,951,623 B2 | 10/2005 | Wu |
| 6,953,340 B2 | 10/2005 | Cao |
| 6,954,270 B2 | 10/2005 | Ostler et al. |
| 6,955,537 B2 | 10/2005 | Cao |
| 6,957,907 B2 | 10/2005 | Fischer et al. |
| 6,969,253 B2 | 11/2005 | Cao |
| 6,971,875 B2 | 12/2005 | Cao |
| 6,971,876 B2 | 12/2005 | Cao |
| 6,974,319 B2 | 12/2005 | Cao |
| 6,976,841 B1 | 12/2005 | Osterwalder |
| 6,979,193 B2 | 12/2005 | Cao |
| 6,979,194 B2 | 12/2005 | Cao |
| 6,981,867 B2 | 1/2006 | Cao |
| 6,981,876 B2 | 1/2006 | Bleckley et al. |
| 6,986,782 B2 | 1/2006 | Chen et al. |
| 6,988,890 B2 | 1/2006 | Cao |
| 6,988,891 B2 | 1/2006 | Cao |
| 6,991,356 B2 | 1/2006 | Tsimerman et al. |
| 6,991,456 B2 | 1/2006 | Plank |
| 6,994,546 B2 | 2/2006 | Fischer et al. |
| 6,994,551 B2 | 2/2006 | Wang et al. |
| 7,001,057 B2 | 2/2006 | Plank et al. |
| 7,011,519 B2 | 3/2006 | Castellini |
| 7,029,277 B2 | 4/2006 | Gofman et al. |
| 7,056,116 B2 | 6/2006 | Scott et al. |
| 7,066,732 B2 | 6/2006 | Cao |
| 7,066,733 B2 | 6/2006 | Logan et al. |
| 7,074,040 B2 | 7/2006 | Kanca |
| 7,077,648 B2 | 7/2006 | Cao |
| 7,086,111 B2 | 8/2006 | Hilscher et al. |
| 7,086,858 B2 | 8/2006 | Cao |
| 7,094,054 B2 | 8/2006 | Cao |
| 7,097,364 B2 | 8/2006 | Wang |
| 7,101,072 B2 | 9/2006 | Takada et al. |
| 7,104,793 B2 | 9/2006 | Senn et al. |
| 7,106,523 B2 | 9/2006 | McLean et al. |
| 7,108,504 B2 | 9/2006 | Cao |

(56) References Cited

U.S. PATENT DOCUMENTS

| | | |
|---|---|---|
| 7,118,563 B2 | 10/2006 | Weckwerth et al. |
| 7,119,515 B2 | 10/2006 | Senn et al. |
| 7,134,875 B2 | 11/2006 | Oxman et al. |
| 7,139,580 B2 | 11/2006 | Stein et al. |
| 7,144,250 B2 | 12/2006 | Fischer et al. |
| 7,153,015 B2 | 12/2006 | Brukilacchio |
| 7,163,181 B2 | 1/2007 | Omps |
| 7,163,318 B2 | 1/2007 | Panagotacos et al. |
| 7,167,824 B2 | 1/2007 | Kallulli |
| 7,178,941 B2 | 2/2007 | Roberge et al. |
| 7,179,860 B2 | 2/2007 | Cao et al. |
| 7,182,597 B2 | 2/2007 | Gill et al. |
| 7,189,983 B2 | 3/2007 | Aguirre et al. |
| 7,192,276 B2 | 3/2007 | Fischer et al. |
| 7,195,482 B2 | 3/2007 | Scott |
| 7,202,489 B2 | 4/2007 | Aguirre et al. |
| 7,202,490 B2 | 4/2007 | Aguirre et al. |
| 7,207,694 B1 | 4/2007 | Petrick |
| 7,210,814 B2 | 5/2007 | Scott et al. |
| 7,210,930 B2 | 5/2007 | Kovac et al. |
| 7,223,270 B2 | 5/2007 | Altshuler et al. |
| 7,224,001 B2 | 5/2007 | Cao |
| 7,250,611 B2 | 7/2007 | Aguirre et al. |
| 7,251,390 B2 | 7/2007 | Fukai et al. |
| 7,252,678 B2 | 8/2007 | Ostler et al. |
| 7,267,457 B2 | 9/2007 | Ostler et al. |
| 7,267,546 B2 | 9/2007 | Scott et al. |
| 7,271,420 B2 | 9/2007 | Cao |
| 7,273,369 B2 | 9/2007 | Rosenblood et al. |
| 7,283,230 B2 | 10/2007 | Ostler et al. |
| 7,294,364 B2 | 11/2007 | Cao |
| 7,300,175 B2 | 11/2007 | Brukilacchio |
| 7,320,593 B2 | 1/2008 | Ostler et al. |
| 7,323,849 B1 | 1/2008 | Robinett et al. |
| 7,329,887 B2 | 2/2008 | Henson et al. |
| 7,410,283 B2 | 8/2008 | West et al. |
| 7,422,598 B2 | 9/2008 | Altshuler et al. |
| 7,443,133 B2 | 10/2008 | Hamada et al. |
| 7,452,924 B2 | 11/2008 | Aasen et al. |
| 7,471,068 B2 | 12/2008 | Cegnar |
| 7,483,504 B2 | 1/2009 | Shapira et al. |
| 7,485,116 B2 | 2/2009 | Cao |
| 7,507,491 B2 | 3/2009 | Finkelshtain et al. |
| 7,530,707 B2 | 5/2009 | Plank et al. |
| 7,530,808 B2 | 5/2009 | Cao et al. |
| 7,624,467 B2 | 12/2009 | Hilscher et al. |
| 7,645,056 B1 | 1/2010 | Mills et al. |
| 7,645,086 B2 | 1/2010 | Zhang et al. |
| 7,651,268 B2 | 1/2010 | Cao et al. |
| 7,654,086 B2 | 2/2010 | Gong et al. |
| 7,661,172 B2 | 2/2010 | Hilscher et al. |
| 7,677,888 B1 | 3/2010 | Halm |
| 7,677,890 B2 | 3/2010 | Turner |
| 7,696,728 B2 | 4/2010 | Cross et al. |
| 7,704,074 B2 | 4/2010 | Jensen |
| 7,712,468 B2 | 5/2010 | Hargadon |
| 7,728,345 B2 | 6/2010 | Cao |
| 7,733,056 B2 | 6/2010 | Hartung et al. |
| 7,758,204 B2 | 7/2010 | Klipstein et al. |
| 7,786,499 B2 | 8/2010 | Cao |
| 7,861,363 B2 | 1/2011 | Moll et al. |
| 7,976,211 B2 | 7/2011 | Cao |
| 7,989,839 B2 | 8/2011 | Dahm |
| 7,995,882 B2 | 8/2011 | Wanninger et al. |
| 8,019,405 B2 | 9/2011 | Weber et al. |
| 8,096,691 B2 | 1/2012 | Mills et al. |
| 8,113,830 B2 | 2/2012 | Gill et al. |
| 8,174,209 B2 | 5/2012 | Bayer et al. |
| 8,203,281 B2 | 6/2012 | Cegnar et al. |
| 8,231,383 B2 | 7/2012 | Gill et al. |
| 8,269,469 B2 | 9/2012 | Cegnar et al. |
| 8,333,588 B2 | 12/2012 | Putz et al. |
| 8,337,097 B2 | 12/2012 | Cao |
| 8,568,140 B2 | 10/2013 | Kovac et al. |
| 8,569,785 B2 | 10/2013 | Cao |
| 8,602,774 B2 | 12/2013 | Wasyluscha |
| 8,653,723 B2 | 2/2014 | Cao et al. |
| 8,834,457 B2 | 9/2014 | Cao |
| 9,066,777 B2 | 6/2015 | Gill |
| 9,072,572 B2 | 7/2015 | Gill et al. |
| 2001/0007739 A1 | 7/2001 | Eibofner et al. |
| 2002/0093833 A1 | 7/2002 | West |
| 2002/0168607 A1 | 11/2002 | Cao |
| 2003/0015667 A1 | 1/2003 | MacDougald et al. |
| 2003/0036031 A1 | 2/2003 | Lieb et al. |
| 2003/0060013 A1 | 3/2003 | Marchant et al. |
| 2003/0081430 A1 | 5/2003 | Becker |
| 2003/0147258 A1 | 8/2003 | Fischer et al. |
| 2003/0148242 A1 | 8/2003 | Fischer et al. |
| 2003/0152885 A1 | 8/2003 | Dinh |
| 2003/0186195 A1 | 10/2003 | Comfort et al. |
| 2003/0215766 A1 | 11/2003 | Fischer et al. |
| 2003/0235800 A1 | 12/2003 | Qadar |
| 2004/0054386 A1 | 3/2004 | Martin et al. |
| 2004/0101802 A1 | 5/2004 | Scott |
| 2004/0117930 A1 | 6/2004 | Townley et al. |
| 2004/0120146 A1 | 6/2004 | Ostler et al. |
| 2004/0152038 A1 | 8/2004 | Kumagai et al. |
| 2004/0181154 A1 | 9/2004 | Peterson et al. |
| 2004/0214131 A1 | 10/2004 | Fischer et al. |
| 2004/0256630 A1 | 12/2004 | Cao |
| 2005/0002975 A1 | 1/2005 | Cao |
| 2005/0033119 A1 | 2/2005 | Okawa et al. |
| 2005/0074723 A1 | 4/2005 | Ostler et al. |
| 2005/0077865 A1 | 4/2005 | Durbin et al. |
| 2005/0082989 A1 | 4/2005 | Jones et al. |
| 2005/0096661 A1 | 5/2005 | Farrow et al. |
| 2005/0099824 A1 | 5/2005 | Dowling et al. |
| 2005/0154081 A1 | 7/2005 | Yin et al. |
| 2005/0158687 A1 | 7/2005 | Dahm |
| 2005/0171408 A1 | 8/2005 | Parker |
| 2005/0174753 A1 | 8/2005 | Cao et al. |
| 2005/0174801 A1 | 8/2005 | Cao |
| 2005/0196721 A1 | 9/2005 | Jackson et al. |
| 2005/0282102 A1 | 12/2005 | Kert |
| 2006/0033052 A1 | 2/2006 | Scott |
| 2006/0040231 A1 | 2/2006 | Quan et al. |
| 2006/0044823 A1 | 3/2006 | Wong et al. |
| 2006/0084028 A1 | 4/2006 | Cheetham et al. |
| 2006/0084717 A1 | 4/2006 | Cohen et al. |
| 2006/0095095 A1 | 5/2006 | Cao |
| 2006/0188835 A1 | 8/2006 | Nagel et al. |
| 2006/0188836 A1 | 8/2006 | Logan et al. |
| 2006/0199144 A1 | 9/2006 | Liu et al. |
| 2006/0240375 A1 | 10/2006 | Soukos et al. |
| 2006/0252005 A1 | 11/2006 | Feinbloom et al. |
| 2006/0271068 A1 | 11/2006 | Cao |
| 2006/0274529 A1 | 12/2006 | Cao |
| 2006/0275732 A1 | 12/2006 | Cao |
| 2006/0275733 A1 | 12/2006 | Cao |
| 2007/0020578 A1 | 1/2007 | Scott et al. |
| 2007/0031777 A1 | 2/2007 | Wang et al. |
| 2007/0037113 A1 | 2/2007 | Scott et al. |
| 2007/0054232 A1 | 3/2007 | Rauchenzauner |
| 2007/0128577 A1 | 6/2007 | Scott et al. |
| 2007/0170444 A1 | 7/2007 | Cao |
| 2007/0224570 A1 | 9/2007 | West et al. |
| 2007/0225658 A1 | 9/2007 | Jensen et al. |
| 2007/0228392 A1 | 10/2007 | Plank et al. |
| 2007/0265607 A1 | 11/2007 | Cao et al. |
| 2007/0279011 A1 | 12/2007 | Jones et al. |
| 2008/0027518 A1 | 1/2008 | Island et al. |
| 2008/0071256 A1 | 3/2008 | Cao et al. |
| 2008/0080184 A1 | 4/2008 | Cao |
| 2008/0086117 A1 | 4/2008 | Cao |
| 2008/0191941 A1 | 8/2008 | Saban et al. |
| 2008/0225019 A1 | 9/2008 | Hsiung |
| 2008/0285302 A1 | 11/2008 | Scott et al. |
| 2008/0311545 A1 | 12/2008 | Ostler et al. |
| 2008/0315829 A1 | 12/2008 | Jones et al. |
| 2009/0011385 A1 | 1/2009 | Jensen et al. |
| 2009/0087393 A1 | 4/2009 | Jensen et al. |
| 2009/0092947 A1 | 4/2009 | Cao et al. |
| 2009/0143842 A1 | 6/2009 | Cumbie et al. |

(56) References Cited

U.S. PATENT DOCUMENTS

| | | |
|---|---|---|
| 2009/0147505 A1 | 6/2009 | Robinett |
| 2009/0155740 A1 | 6/2009 | Jensen et al. |
| 2009/0208894 A1 | 8/2009 | Orloff et al. |
| 2009/0227875 A1 | 9/2009 | Cao et al. |
| 2009/0238779 A1 | 9/2009 | Jensen et al. |
| 2009/0271936 A1 | 11/2009 | Walanski et al. |
| 2010/0004640 A1 | 1/2010 | Cao et al. |
| 2010/0117560 A1 | 5/2010 | Cao |
| 2010/0173267 A1 | 7/2010 | Cao et al. |
| 2010/0273123 A1 | 10/2010 | Mecher |
| 2011/0070553 A1 | 3/2011 | Stempfle et al. |
| 2011/0143304 A1 | 6/2011 | Jamnia et al. |
| 2012/0230017 A1 | 9/2012 | Duffy |
| 2014/0038125 A1 | 2/2014 | Logan et al. |
| 2014/0051031 A1 | 2/2014 | Kovac et al. |

FOREIGN PATENT DOCUMENTS

| | | |
|---|---|---|
| CA | 2298993 A1 | 9/2000 |
| DE | 2315709 A1 | 10/1974 |
| DE | 2927260 A1 | 2/1980 |
| DE | 2842938 A1 | 4/1980 |
| DE | 3411996 A1 | 10/1985 |
| DE | 3706852 A1 | 10/1987 |
| DE | 9017070 U1 | 4/1992 |
| DE | 4211233 A1 | 8/1993 |
| DE | 29511927 U1 | 1/1997 |
| DE | 19624087 A1 | 12/1997 |
| DE | 19803755 A1 | 8/1999 |
| EP | 000266038 A2 | 5/1988 |
| EP | 000320080 A1 | 6/1989 |
| EP | 0531438 A1 | 3/1993 |
| EP | 000568666 A1 | 11/1993 |
| EP | 000591613 A1 | 4/1994 |
| EP | 000672435 A1 | 9/1995 |
| EP | 000678282 A2 | 10/1995 |
| EP | 000709698 A1 | 5/1996 |
| EP | 000736307 A2 | 10/1996 |
| EP | 000740567 A1 | 11/1996 |
| EP | 000750889 A1 | 1/1997 |
| EP | 000755662 A1 | 1/1997 |
| EP | 000780101 A2 | 6/1997 |
| EP | 000780103 A2 | 6/1997 |
| EP | 000830850 A1 | 3/1998 |
| EP | 000830851 A1 | 3/1998 |
| EP | 000830852 A1 | 3/1998 |
| EP | 000879582 A2 | 11/1998 |
| EP | 000880945 A2 | 12/1998 |
| EP | 000884025 A1 | 12/1998 |
| EP | 000885025 A1 | 12/1998 |
| EP | 000959803 A1 | 12/1999 |
| EP | 000998880 A2 | 5/2000 |
| EP | 001031326 A1 | 8/2000 |
| EP | 001090607 A1 | 4/2001 |
| EP | 001090608 A1 | 4/2001 |
| EP | 001093765 A2 | 4/2001 |
| EP | 001103232 A1 | 5/2001 |
| EP | 001112721 A1 | 7/2001 |
| EP | 001138276 A1 | 10/2001 |
| EP | 001138349 A2 | 10/2001 |
| EP | 001206923 A1 | 5/2002 |
| EP | 001228738 A1 | 8/2002 |
| EP | 001253547 A2 | 10/2002 |
| EP | 001374797 A1 | 1/2004 |
| EP | 001843079 A2 | 10/2007 |
| EP | 2058636 A2 | 5/2009 |
| FR | 2629999 A1 | 10/1989 |
| GB | 1570507 A | 7/1980 |
| GB | 002212010 A | 7/1989 |
| GB | 002218636 A | 11/1989 |
| GB | 002329756 A | 3/1999 |
| GB | 002385137 A | 8/2003 |
| JP | 7240536 | 9/1985 |
| JP | 8141001 | 6/1996 |
| JP | H06285508 A | 6/1996 |
| JP | 910238 | 1/1997 |
| JP | 928719 | 4/1997 |
| JP | 9187825 | 7/1997 |
| JP | 1033573 | 2/1998 |
| JP | 10245245 | 9/1998 |
| JP | 11267140 | 1/1999 |
| JP | 2000312688 | 11/2000 |
| JP | 2001522635 | 11/2001 |
| JP | 2002125984 | 5/2002 |
| JP | 2002320683 | 5/2002 |
| JP | 2002200100 | 7/2002 |
| JP | 2003093405 | 4/2003 |
| JP | 2003524501 A | 8/2003 |
| JP | 2003288201 | 10/2003 |
| JP | 2004040998 A | 2/2004 |
| JP | 2004355852 | 12/2004 |
| JP | 2005168231 A | 6/2005 |
| JP | 2006149190 A | 6/2006 |
| JP | 2007509669 A | 4/2007 |
| JP | 2007128667 | 5/2007 |
| JP | 2007514454 | 6/2007 |
| JP | 2007516689 A | 6/2007 |
| JP | 2011135973 A | 7/2011 |
| WO | 8301311 | 4/1983 |
| WO | 8404463 | 11/1984 |
| WO | 9202275 | 2/1992 |
| WO | 9309847 | 5/1993 |
| WO | 9321842 | 11/1993 |
| WO | 9507731 | 3/1995 |
| WO | 9519810 | 7/1995 |
| WO | 9526217 | 10/1995 |
| WO | 9736552 | 10/1997 |
| WO | 9737722 | 10/1997 |
| WO | 9739880 A2 | 10/1997 |
| WO | 9746279 | 12/1997 |
| WO | 9746280 | 12/1997 |
| WO | 9803131 | 1/1998 |
| WO | 9803132 | 1/1998 |
| WO | 9804317 | 2/1998 |
| WO | 9836703 | 8/1998 |
| WO | 9909071 | 2/1999 |
| WO | 9911324 | 3/1999 |
| WO | 9916136 | 4/1999 |
| WO | 9920346 | 4/1999 |
| WO | 9935995 | 7/1999 |
| WO | 9937239 | 7/1999 |
| WO | 0002491 | 1/2000 |
| WO | 0013608 | 3/2000 |
| WO | 0014012 | 3/2000 |
| WO | 0015296 | 3/2000 |
| WO | 0017569 A1 | 3/2000 |
| WO | 0041726 | 7/2000 |
| WO | 0041767 | 7/2000 |
| WO | 0041768 | 7/2000 |
| WO | 0043067 | 7/2000 |
| WO | 0043068 | 7/2000 |
| WO | 0043069 A1 | 7/2000 |
| WO | 0045733 A1 | 8/2000 |
| WO | 0067048 A2 | 11/2000 |
| WO | 0067660 A1 | 11/2000 |
| WO | 0103770 A1 | 1/2001 |
| WO | 0119280 A1 | 3/2001 |
| WO | 0124724 A1 | 4/2001 |
| WO | 0154770 A1 | 8/2001 |
| WO | 0160280 A1 | 8/2001 |
| WO | 0164129 A1 | 9/2001 |
| WO | 0168035 A2 | 9/2001 |
| WO | 0169691 A1 | 9/2001 |
| WO | 0206723 A1 | 1/2002 |
| WO | 0209610 A1 | 2/2002 |
| WO | 0211640 A2 | 2/2002 |
| WO | 0232505 A1 | 4/2002 |
| WO | 0233312 A2 | 4/2002 |
| WO | 0249721 A1 | 6/2002 |
| WO | 02056787 A2 | 7/2002 |
| WO | 02069839 A1 | 9/2002 |
| WO | 02080808 A1 | 10/2002 |
| WO | 03083364 A1 | 10/2003 |
| WO | 2005006818 | 1/2005 |

(56) References Cited

FOREIGN PATENT DOCUMENTS

| WO | 2005043709 A1 | 5/2005 |
|----|---------------|--------|
| WO | 2006014363 A2 | 2/2006 |
| WO | 2006014597 A1 | 2/2006 |
| WO | 2009134885 A1 | 11/2009 |
| WO | 2010029519 A2 | 3/2010 |
| WO | 2010115082 A1 | 10/2010 |

OTHER PUBLICATIONS

Davidson-Kaban, Saliha S. et al., The Effect of Curing Light Variations on Bulk Curing and Wall-to-Wall Quality of Two Types and Various Shades of Resin Composites, ; Dent. Mater. 13: 344-352, Nov. 1997.

Feltzer, A. J. et al., Influence of Light Intensity on Polymerization Shrinkage and Integrity of Restoration-Cavity Interface, Eur. J. Oral Sciences, 103: 322-326, 1995.

Kanca, III, John and Suh, Byoung I., Pulse Activation: Reducing Resin-Based Composite Contraction Stresses at the Enamel Cavosurface Margins, Am. J. Of Dentistry, 12(3), 107-112, 1999.

Kato, Hiromasa, Relationship Between the Velocity of Polymerization and Adaptation to Dentin Cavity Wall of Light-Cured Composite, Dental Materials J. 6(1): 32-37, 1987.

Koran, Peter and Kurschner, Ralf, Effect of Sequential versus Continuous Irradiation of a Light-Cured Resin Composite on Shsrinkage, Viscosity, Adhesion, and Degree of Polymerization, Am. J. of Dentistry, 11, No. 1, 17-22, 1998.

LumiLeds Lighting LLC, Luxeon™ Power Light Sources of the Future, Jan. 2001—Mike Holt.

LumiLeds Lighting LLC, Application Note 1149-5, Secondary Optics Design Considerations for Super Flux LEDs, Copyright © 2000 LumiLeds Lighting, Obsoletes Publication No. 5968-1215E, Publication No. AN06 (3/O0).

LumiLeds Lighting LLC, LED Application Note Dental Light Curing, LumiLeds Lighting Publication No. XXX(03.01), Copyright © 2000.

LumiLeds Lighting LLC, Concept Evaluation Data Luxeon™ Star 5-Watt, Luxeon™ 5-Watt Prelminary Target Data Sheet, Publication No. JP10 (Jan. 2002).

LumiLeds Lighting LLC, Application Bulletin AB XXX, Luxeon™ Data Sheet, Publication No. xxxx-xxxx.

LumiLeds Lighting LLC, Lumen Maintenance of White Luxeon™ Power Light Sources, Application Brief AB07, LumiLeds Lighting, US LLC.

Luxeon Dental Technical Data, Power Light Source, ; Apr. 2002.

Mayes, Joe H., Curing Lights: An Overview, Unknown, p. 15-17.

Mehl, et al., Softstartpolymerisation von Kompositen in Klasse-V-Kavitatent, Dtsch Zhnarzl Z. 52/1997, pp. 824-827 (in German).

Mehl, A. et al., Physical Properties and Gap Formation of Light-Cured Composites With and Without 'Softstart-Polymerization', J. of Dentistry, 25, 321-330, 1997.

Mehl, et al., 496 The Influence of Pre-Curing on the Material Properties of Composite Resins, Journal of Dental Research, vol. 74, 1995, Special Issues S.462 (abstract).

Mehl, et al., Soft Start Polymerization of Composites in Class V Cavities, Dtsch Zhnarztl Z. 52/1997, pp. 824-827.

Mills, Robin W., et al., Blue LED's for Curing Polymer-Based Dental Filling Materials, LEO's Newsletter, Jun. 1998.

Mills, R. W., et al., Optical Power Outputs, Spectra and Dental Composite Depths of Cure, Obtained with Blue Light Emitting Diode (LED and Halogen Light Curing Units (LCU's), Oct. 26, 2002.

Reinhardt, et al., Unischerheiten bei der Prufung von Photopolymerisation, Dtsch zahnarzl Z. 36,635-640, 1981 (in German).

Reinhardt, et al., Uncertainties ini the Testing of Photopolymers, Dtsch zahnarzl Z. 36, 635-640, 1981 (English Translation of cite No. 5 above).

Sakaguchi, Ronald L. and Berge, Hong Xu, ; Sakaguchi & Berge, Reduced Light Energy Density Decreases Post-Gel Contraction While Maintaining Degree of Conversion in Composites, J. of Dentistry, 26, 695-700, 1998.

Schlager, Kenneth J., Ignatius, Ronald W., ; An LED-Array Light Source for Medical Therapy, ; SPIE vol. 1892 Medical Lasers and Systems II (1993) p. 26-35.

Swift Jr., Edward J. et al., Ed., Contemporary Photocuring Issues, Part II, J. Esthetic Dentistry, 12 (1), 50-57, 2000.

Tarle, Z. et al., The Effect of the Photopolymerization Method on the Quality of Composite Resin Samples, ; J. of Oral Rehab. 25: 436-442, 1998.

TIR Technologies, Inc., Miniaturized TIR lenses for Light Emitting Diodes, TIR Technical Publication, pp. 1-14, 1992.

Uno, Shigeru and Asmussen, Erik, Marginal Adaptation of a Restorative Resin Polymerized at Reduced Rate, ; Scand J. Dent. Res. 1991; 99: 440-4.

2-Page International Search Report for EP07020186 mailed Jan. 7, 2009.

Six-page Partial European Search Report for Application No. EP08021597 dated Aug. 27, 2009.

Seventeen-Page International Search Report mailed Sep. 20, 2010 for International Application No. PCT/US2010/029756.

George W. Gaines, Lieutenant Colonel, USAF, DC & Curtis D. Wyrauch, Major, USAG, DC, A New Generation of Visible-Light Curing Units, USAF School of Aerospace Medicine, Final Report for Period Oct. 1987-Sep. 1988.

Thirteen-Page European Search Report mailed Nov. 21, 2014 for European Patent Application No. EP14172118.

Two-Page Annex to Partial International Search Report dated Jun. 28, 2010.

Fourteen-page Supplemental International Search Report mailed Sep. 20, 2010 for International Application No. PCT/US2010/029756.

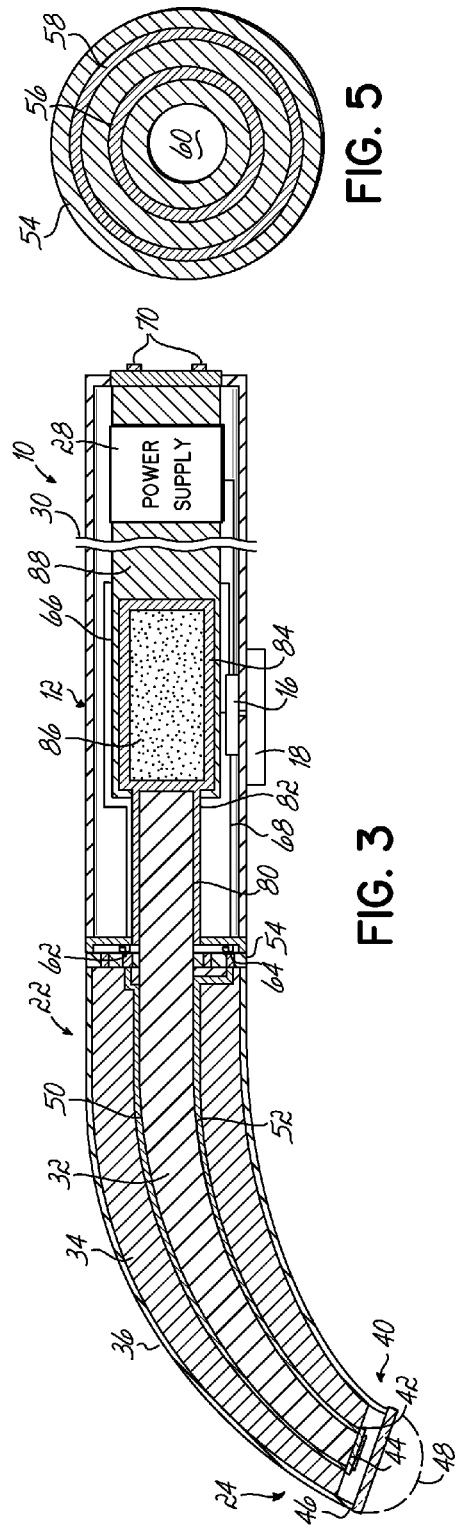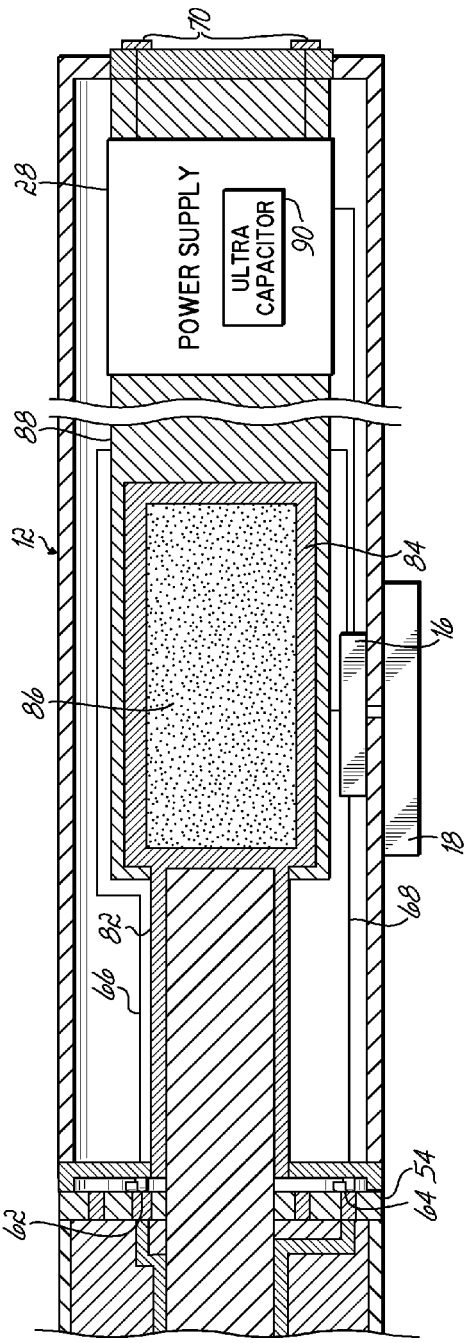

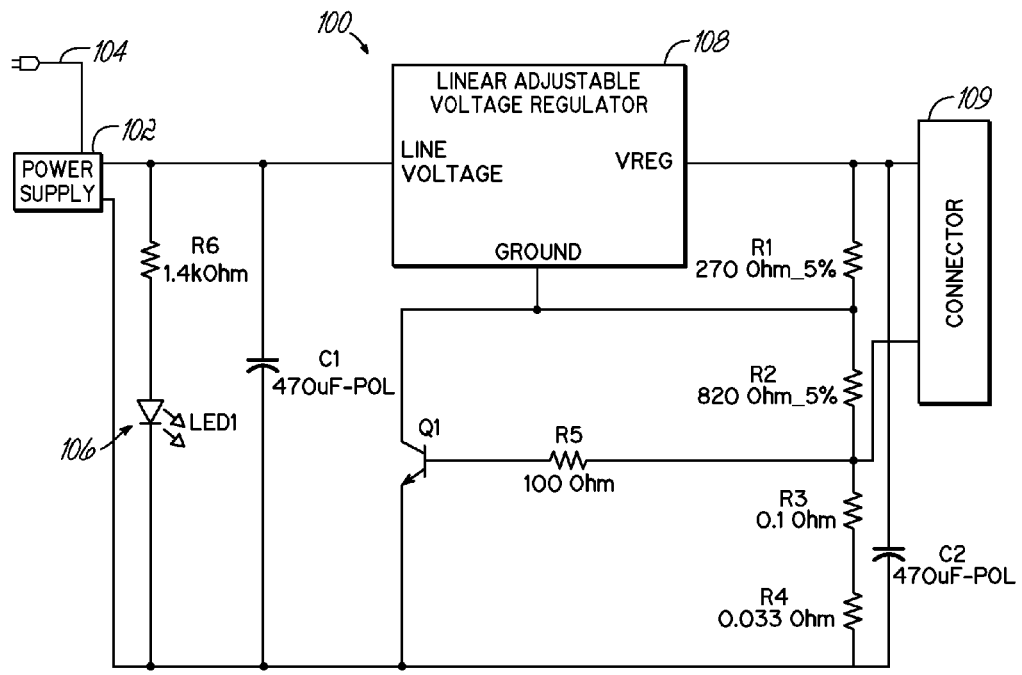
FIG. 6
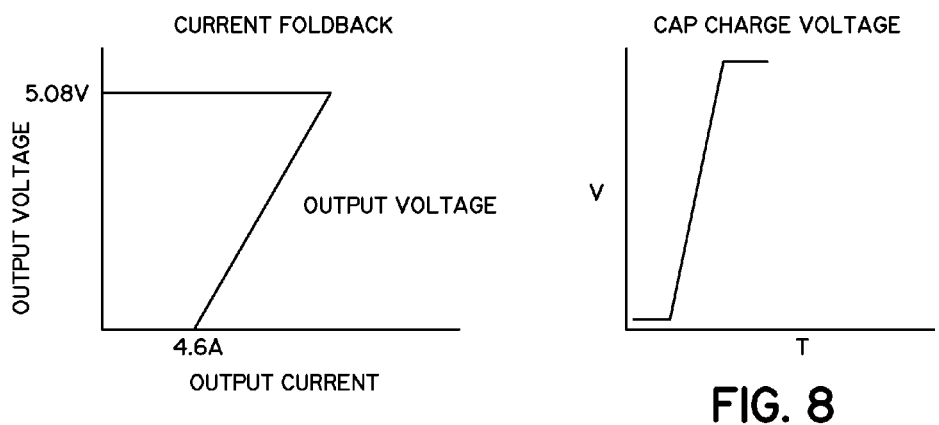
FIG. 7
FIG. 8

CURING LIGHT DEVICE

CROSS-REFERENCE TO RELATED APPLICATIONS

This Application is a continuation Application of U.S. patent application Ser. No. 12/752,335, filed Apr. 1, 2010, entitled "CURING LIGHT DEVICE", which claims the benefit of U.S. Patent Application Ser. No. 61/166,130, filed Apr. 2, 2009, entitled "CURING LIGHT DEVICE", which applications are incorporated herein by reference in their entireties.

FIELD OF THE INVENTION

This invention relates to illumination or light devices, and more specifically to an illumination device that is used for oral and dental applications and provides light to illuminate and to cure light-curable compounds in dental applications.

BACKGROUND OF THE INVENTION

Many illumination devices or light devices exist for use in dental and oral applications. One specific category of dental illumination devices is directed to hand-held devices that are held in proximity to the mouth of the patient to illuminate an area within the patient's mouth for various reasons. One particular usage is directed to curing light-curable compounds in the mouth. While suitable hand-held light devices exist for dental applications, there are often various drawbacks associated with such light devices, particularly with respect to dental curing lights.

Many such dental lights have a body, which contains the light elements, such as light-emitting diodes (LED). A tapered and curved light guide, then interfaces with the end of the body and the light-emitting elements to capture the light and direct it where desired. Generally, such light guides are bundles of fiber-optic elements, which operate to capture the light in the device, away from the patient's mouth, and then forward that light to a tip that may be placed at the area of interest within a patient's mouth. While such light guides operate in a suitable manner, they are also very inefficient. Almost half of the light generated in the device is lost in the transmission from its source down to the tip, through the light guide. Such inefficiency requires a significantly large light engine to generate the light needed at the curing site, such as for curing a compound. In turn, heat is generated, which must be properly removed and directed away from the light engine. The greater the output required by the light engine, the more heat that must be addressed.

Another issue associated with such dental lights is their sterilization. As may be appreciated, the tip of the dental light is generally brought into proximity or into actual contact with the mouth of the patient or some portion of the mouth. Thus, the tip of the light device is exposed to various germs and bacteria. Accordingly, in order to prevent the propagation of germs or infection between patients, dental instruments are often sterilized, such as by being autoclaved at a very high temperature. While suggestions and some attempts have been made in the art to move the light engine of a dental light closer to the operating tip, such attempts have not thoroughly addressed the issue of sterilization. For example, the temperature at which autoclaving is achieved is potentially damaging to a light engine, such as the light-emitting elements in an LED array. Accordingly, the issue of sterilization has not been adequately addressed by existing dental lights, such as dental curing lights.

Another drawback to existing dental lights is directed to their need for a power source. Often times, such lights are actually plugged into a base that then couples to an AC source, such as a wall outlet. Some are connected directly to an AC wall outlet. Some portable dental light devices are not attached to a base, but rather utilize batteries, such as rechargeable batteries. However, rechargeable batteries require a significant amount of time to charge, and thus, there may be some valuable down time required for the dental light, when it might otherwise be put to use. Furthermore, existing battery charging technology uses batteries that are subject to a somewhat limited number of charge cycles. Their continued ability to take and maintain a charge is reduced over time and usage. After a somewhat limited number of cycles, the batteries have to be replaced. Thus, there is still a need to address power issues in portable curing lights.

As such, various drawbacks remain in the field of dental lights, particularly dental curing lights, which are not addressed by the current art.

BRIEF DESCRIPTION OF THE DRAWINGS

FIG. 3 is a side cross-sectional view of the light device of FIG. 1 showing the tip structure engaging the housing.

FIG. 4 is a partial cross-sectional view of an alternative embodiment of the light device of the invention.

FIG. 5 is a plan view of an end cap structure for a tip structure of the invention.

FIG. 6 is a circuit schematic for a charging circuit to be used to charge the invented light device.

FIG. 7 is a graphical depiction of the curve for operation of the circuit of FIG. 7.

FIG. 8 is a graphical depiction of the charging of the ultracapacitors according to an embodiment of the invention.

DETAILED DESCRIPTION OF THE DRAWINGS

The accompanying drawings, which are incorporated in and constitute a part of this specification, illustrate embodiments of the invention and, together with a general description of the invention given below, serve to explain the principles of the invention.

Figure 1:
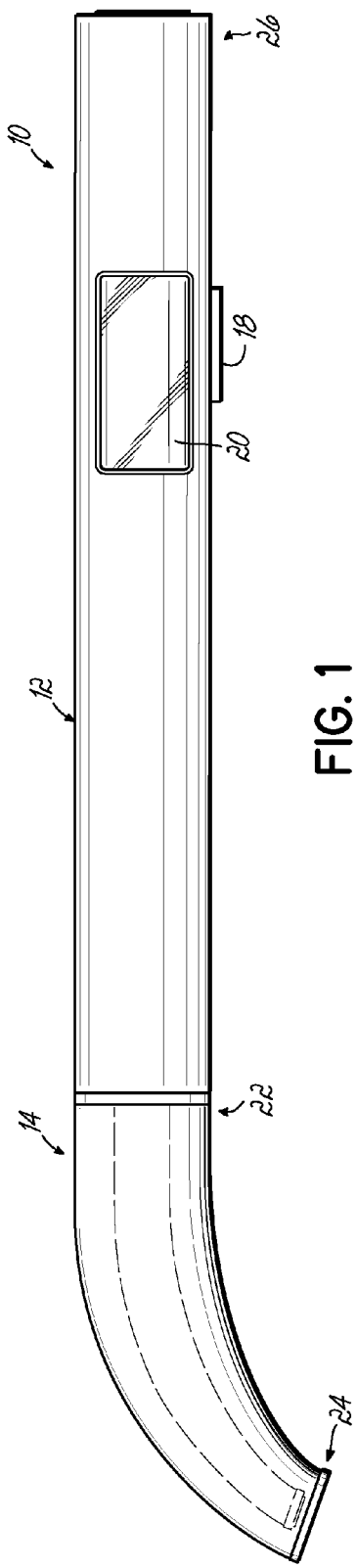
FIG. 1 is a side view of a light device incorporating features of the present invention.
Figure 1A:
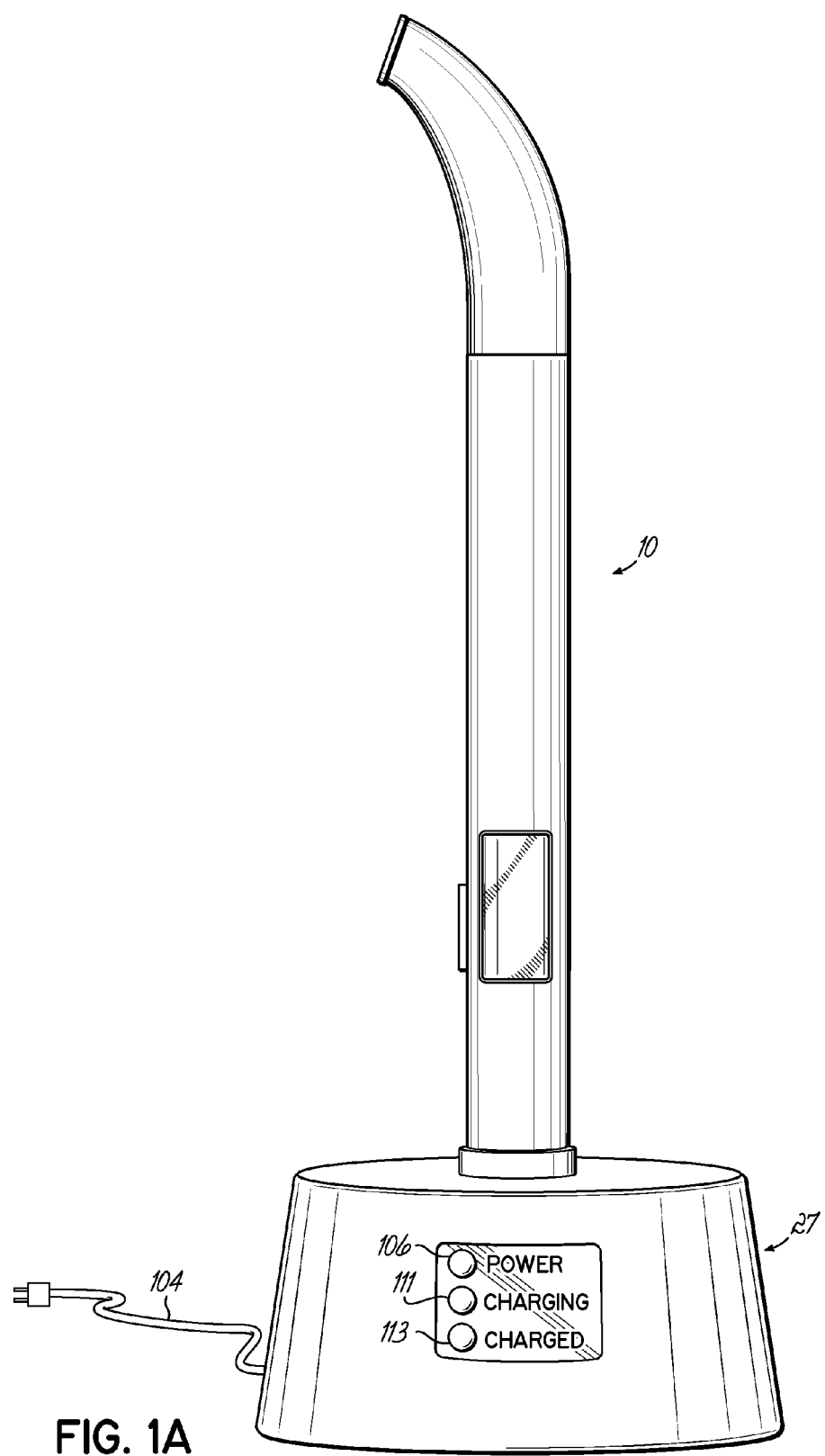
FIG. 1A is a perspective view of a light device in a charging base.

FIG. 1 illustrates one embodiment of a light device 10 of the present invention. While one embodiment of light device 10 might be used for curing, other uses are also anticipated, such as illumination, tooth whitening, or other treatment applications. Thus, the present invention is not limited to the particular use described herein for an exemplary embodiment. Curing device 10 includes the housing 12 and a tip structure 14 that is removably coupled to the housing 12. In accordance with one aspect of the invention, as discussed further hereinbelow, the tip structure 14 may be removed so that it may be separately autoclaved from the overall device. Device 10 also includes suitable control electronics 16 (See FIG. 2) with external controls 18 that may include buttons, switches, or other suitable manual controls for controlling device 10. A display device 20 might also be utilized and may include a screen, individual light elements, or other graphical elements for providing a visual display of the operation of device 10. For example, the operational mode or setting of the device, the selectable curing times, the remaining curing time, the charging or power status, and diagnostic graphics might also be illustrated utilizing a visual display 20. The tip structure 14 includes a proximal end 22 that is removably coupled with housing 12, and a distal end 24, which is placed within the mouth of a patient for curing a light-curable compound, in accordance with the invention. The base 26 of housing 12 might be coupled to a suitable external power supply, such as an AC or DC source in the form of a charging base or dock 27, as shown in FIG. 1A, for charging rechargeable internal elements of power supply circuit 28 of the device 10 (See FIG. 2). Base 26 might also be configured to fit within a suitable structure, such as a standalone, table-mounted base, a mounting structure for mounting it on a wall, pole, or chair, or might be incorporated in a portion of a dental chair for holding and charging the curing device 10.

Figure 2:
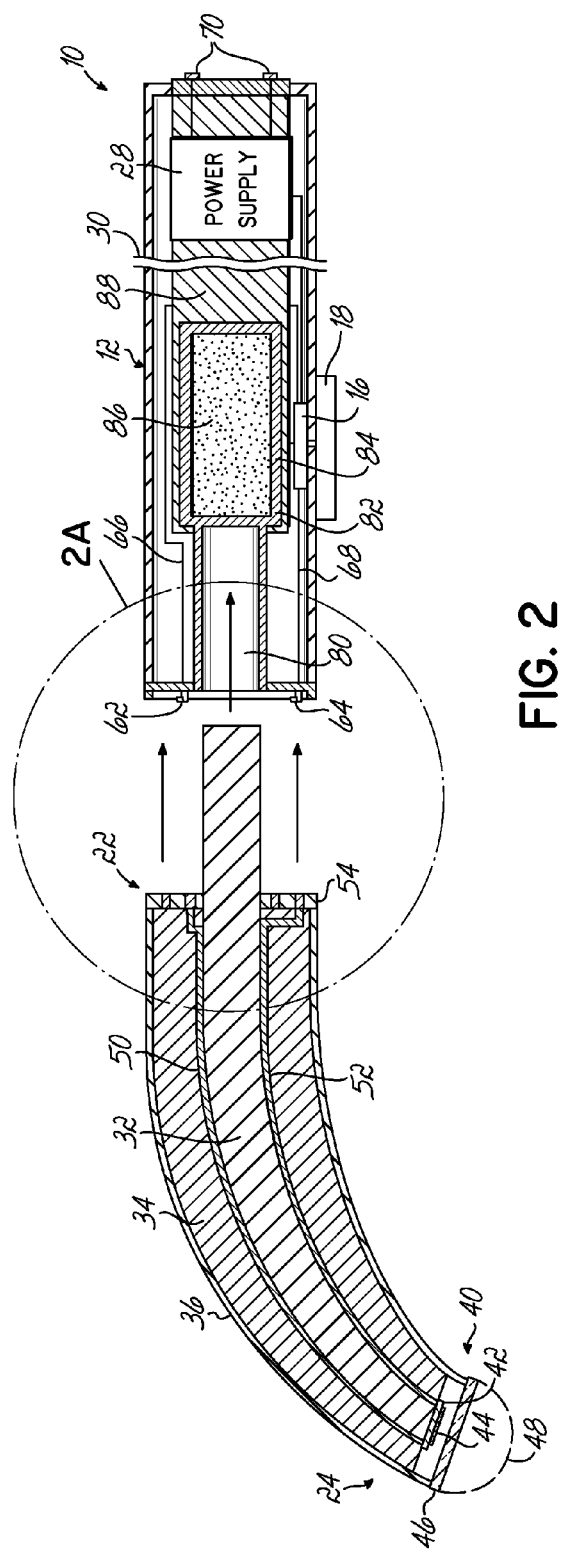
FIG. 2 is an exploded cross-sectional view of the light device of FIG. 1.
Figure 2A:
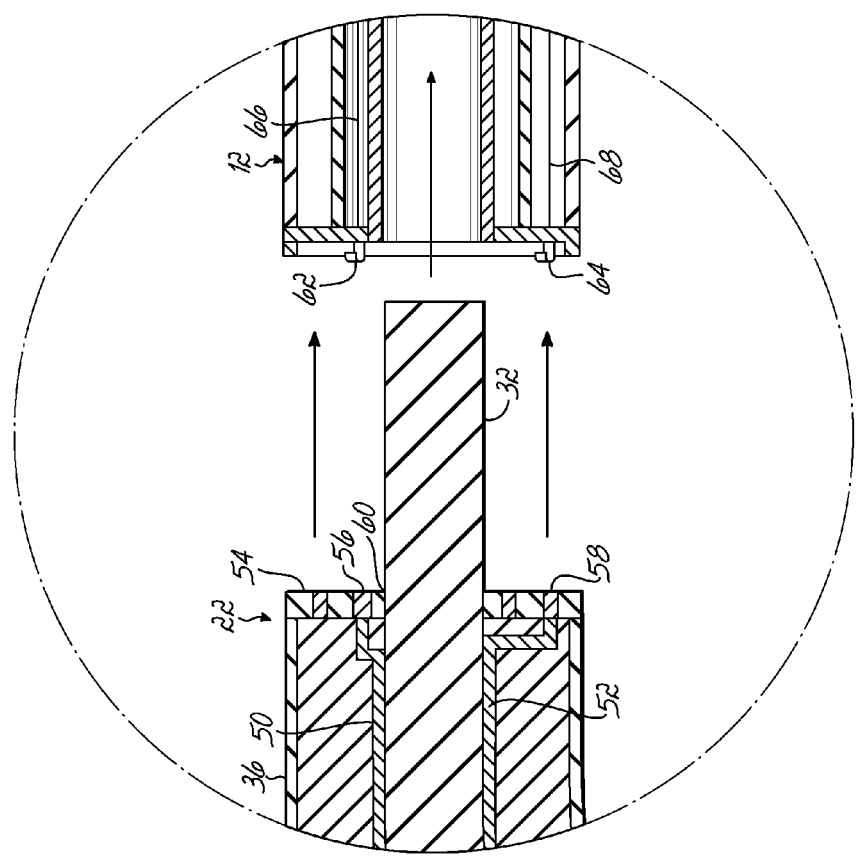
FIG. 2A is an enlarged view of a portion of FIG. 2.

FIGS. 2 and 2A illustrate cross-sectional views of device 10, showing the interface between the tip structure 14 and housing 12.

FIG. 3 illustrates the tip structure 14 engaging the housing. In the figures, section lines 30 are shown indicating a removable portion of the housing 12 for illustrative purposes. The housing 12, as well as the tip structure 14, may be sized as appropriate for a hand-held curing device that may be manipulated to position the distal end 24 of the device in the mouth of a patient, or otherwise proximate to light-curable material and compounds.

Tip structure 14 includes a heat sink structure or element 32 that extends in the tip structure from the proximal end 22 to the distal end 24. In one embodiment of the invention, as illustrated in FIGS. 2 and 2A, the heat sink 32 extends past the proximal end 22 of the tip structure 14 to engage the housing 12 for appropriate thermal transfer of heat from a curing light device. The heat sink may be made from a suitable heat-transfer or heat-conducting material, such as a metal (e.g. copper) or aluminum. Alternatively, a high thermal conductivity material such as Pyrolytic Graphite sheets (PGS) might be used for heat sink 32. In one embodiment, the heat sink 32 is an elongated copper tube formed in an appropriate shape for positioning inside the tip structure 14. Suitable thermal insulation material 34 surrounds the heat sink 32. Tip structure 14 includes a body 36 that houses the elements of the tip structure, and is appropriately sealed at its proximal and distal ends 22 and 24, as discussed further hereinbelow. The body 36 is made from an autoclavable material in accordance with one aspect of the invention. As noted above, it is desirable to sterilize certain reusable dental elements, such as those that are used in or inserted into or onto or proximate to the mouth of a patient. Past curing light devices have not been autoclavable to the degree desired by dental professionals. The present invention provides the tip structure enclosed within a sealed body 36 made from an autoclavable material that is able to withstand high temperature autoclaving, such as above 121° C., thus making the entire tip structure, including the light-emitting device or engine therein, autoclavable as well.

In one embodiment of the invention, the autoclavable body 36 is formed of a suitable metal, such as stainless steel. Alternatively, the body 36 might be formed of a ceramic, glass, or porcelain material that is able to withstand the temperatures associated with autoclaving. Generally, the body 36 will be formed to a suitable shape in conjunction with the heat sink 32 and insulation material 34. For example, the heat sink 32 and insulation material 34 might be formed and the body 36 then formed by coating with the ceramic, glass porcelain, or other autoclavable material. In the embodiment illustrated in the figures, the tip structure 14 is appropriately curved from manipulation at a curing site, such as the mouth of a patient, and thus, the body 36 is formed in a curved fashion as well.

Coupled at the distal end of the heat sink 32 is a light-emitting device, or light-emitting engine 40. Such light-emitting devices may include one or more LED elements that are known for curing light-curable compounds, such as dental compounds, and are available from various manufacturers. High power LED elements are one suitable type of elements for the inventive device. For example, a high-power dental LED might be used. The light-emitting engine might use a single LED element or a plurality of elements in an array. Generally, for curing purposes, the light-emitting device will emit a light in a particular desired wavelength for curing a light-curable compound. For various dental compounds, a suitable light is in the wavelength range of 400-500 nanometers, or the blue light range. For other uses of the inventive light, such as for examination of the oral regions to detect caries, illuminate areas, and provide cancer screening, other wavelengths might be used.

However, in accordance with another aspect of the invention, various different tip structures 14 may be readily removed and inserted into the housing 12 so that multiple different tip structures might be utilized with a single housing 12. To that end, the light-emitting devices of the various tip structures might be directed to other applications, such as to whiten teeth, or for illumination within the mouth of a patient, but would still be operated with the same housing 12 and its controls. As such, the present invention is not limited to a specific type of lighting device or use, and various different tip structures 14 might be utilized with light-emitting devices that emit light in an appropriate range of wavelengths for different uses, such as curing, whitening, illuminating, screening, etc.

Such light-emitting devices or light engine 40 generally include a base or substrate 42 that supports one or more light-emitting structures, or semi-conductor junctions, such as in the form of light-emitting diodes or LEDs. A single light-emitting structure might be utilized or an array of structures might be arranged on substrate 42 for providing device 40, depending upon the power of the structures or elements. High power LED elements may be used for example. The light-emitting device 40 is able to withstand high temperatures, and thus, utilizes high-temperature structures, or LED's. Substrate 42 is adhered directly to the distal end of heat sink 32 utilizing a high-temperature adhesive or cement. The direct coupling of the light-emitting device 40 to the heat sink 32 provides optimum thermal coupling for removal of the heat generated by the light-emitting structures 44 or substrate 42.

To seal the distal end 24 of housing 36, a glass window 46 or other transparent element is solder-sealed around its periphery to housing 36, as shown in FIGS. 2 and 3. The transparent element is configured to allow light to pass out of the distal end of the housing. To that end, the glass window 46 might include metalized portions around its periphery for proper solder-sealing to the housing 36 utilizing a high-temperature solder, or other appropriate high-temperature adhesive. Generally, the light-emitting device 40 operates with a lens 48 over the LEDs or other light-emitting structures in order to focus the light from those structures. A window 46 is illustrated in FIG. 2. Alternatively, a separate lens 48 might be sealed to the end of the housing 36 instead of a window 46. The lens 48 may be appropriately shaped for focusing light from light-emitting device 40.

To power the light-emitting device 40, the present invention utilizes high-temperature flexible circuits, or flex circuits 50, 52. The flex circuits extend generally along the inside of the tip structure proximate the heat sink 32. The flex circuits are flexible, and thus, may follow the contour or shape of the heat sink 32. In one embodiment of the invention, suitable traces or channels might be formed in the heat sink 32 for placement of the flex circuits 50, 52. The flex circuits 50, 52, in turn, couple to a ceramic end cap 54, with suitable electrically-conductive elements, such as traces, thereon for coupling to the flex circuits, and ultimately to a power supply and control circuits, as discussed further below.

Referring now to FIG. 2A, the proximal end 22 of the tip structure 14, and particularly the proximal end of housing 36, is sealed utilizing a ceramic end cap 54 that has rotational circuit traces 56, 58 formed therein, as illustrated in FIG. 5. Specifically, in one particular feature of the invention, the tip structure 14 is rotatably coupled with housing 12. To facilitate such rotation, while maintaining the delivery of electrical signals to the light-emitting device 40, device 10 of the invention incorporates circular electrically-conductive elements or circuit traces 56, 58 formed on or in the end cap 54. As illustrated in FIG. 5, the circuit traces 56, 58 generally follow the shape of the end cap, and have a generally circular shape. Furthermore, end cap 54 has an appropriate center opening 60 formed therein for passage of the heat sink 32, as illustrated in FIG. 2A. As illustrated in FIG. 2A, the innermost circuit trace 56 is illustrated is being electrically-coupled to the flex circuit 50. Similarly, the outer circuit trace 58 on the end cap 54 is coupled with flex circuit 52. End cap 54 may be a ceramic end cap of a suitable ceramic material, such as aluminum oxide. The ceramic cap may be adhered to the body 36. If the body is metal, the edge of ceramic cap 54 may be metalized for soldering the cap to the end of the body. Alternatively, if the body is made from glass, a suitable high-temperature adhesive might be utilized to couple the end cap to the glass body.

As illustrated in FIGS. 2A and 5, the metal traces 56, 58 are formed through end cap 54 to present a connection for the flex circuits at the distal end of the tip structure. When coupled with or plugged into housing 12, as illustrated in FIG. 2A, the flex circuits 50, 52 via the ceramic end cap 54 are coupled to a suitable power supply circuit and controls. Specifically, spring contacts 62, 64 are mounted at the end of housing 12 that interfaces with tip structure 14. Those spring contacts 62, 64 are coupled through appropriate connections or circuits 66, 68 back to a suitable power supply circuit 28. The supplied power may then be controlled via suitable control circuit 16, such as to control the intensity of the light-emitting device, the duration of its illumination, and various other parameters associated with the operational modes of device 10. Housing 12 contains suitable control circuitry 16 and a power supply circuit 28, along with the various electrical connections/circuits 66, 68 for powering the tip structure 14 and the light-emitting device 40 at its distal end. Power supply circuit 28, through contacts 70 may be coupled to an external supply of power, such as an AC source or a DC source, for charging elements of the power supply. For example, as is illustrated in FIG. 1A, a base 27 might hold or dock device 10 for recharging purposes. In one embodiment of the invention, the power supply circuit includes rechargeable supply elements, such as a battery, which may be charged and removed from the external power source to be manipulated by an operator. In an alternative embodiment of the invention, as discussed below with respect to FIG. 4, an ultracapacitor element or circuit might be utilized to provide the desired power for the light-emitting device 40. Housing 12 may be formed of any suitable material, such as plastic or metal, or some other rigid material.

As illustrated in FIG. 3, when the tip structure 14 is coupled to housing 12, the contacts 62, 64 engage the circuit elements or traces 56, 58 respectively in the end of the tip structure. This electronically couples the light-emitting device with the power supply circuit. Because of the unique circular pattern of the traces, the tip structure 14 may be rotated in a range of 0°-360°, while the contacts 62, 64 still maintain connection to the traces 56, 58. Alternatively, the circular conductive element might only be contacted over some circular range less than 360°, but still allow at least partial rotation. In that way, the tip structure may be rotated without jeopardizing the electrical connection between the housing 12 and the tip structure 14. Although the electrically-conductive elements 56, 58 are illustrated as formed on the tip structure and the contact elements 62, 64, as positioned on the housing, their relative position might be reversed with elements 56, 58 on housing 12 and elements 62, 64 on tip structure 14. That is, the electrically-conductive elements or traces 56, 58 and contact elements 62, 64 may be positioned on either of the opposing housing and tip structure to pass power between the two. In an alternative embodiment, alternate pins and sockets might be used between the housing and tip structure to electrically couple the light-emitting device and power supply circuit.

At the same time, the proximal end of the heat sink 32 engages a suitable channel 80 formed in housing 12. The channel 80 is formed by an additional or secondary heat sink structure or element 82, which is preferably formed of a suitable metal, such as aluminum. In addition to the channel 80, the heat sink 82 includes a reservoir portion 84, which contains additional heat sink material. That reservoir portion might be all metal to form a metal heat sink. In accordance with one embodiment of the invention, the reservoir portion 84 might be made of metal, but then contains an amount of phase change material 86. Phase change material absorbs the heat from the secondary heat sink structure 82, and changes phase upon such absorption. For example, one suitable phase change material might be a paraffin wax that melts as it absorbs heat. This allows a suitable delay in the temperature rise of the light-emitting device 40 to provide a safe temperature level for the light-emitting device and the overall tip structure during normal usage. Other phase change materials might also be contained within the reservoir portion 84 of the secondary heat sink structure 82, and thus, the present invention is not limited to a particular phase change material 86.

As illustrated in FIG. 3, when the tip structure 14 is plugged into, or otherwise coupled to or engaged with, housing 12, the heat sink 32 engages the secondary heat sink structure 82 such that the end of the heat sink 32 is inserted into channel 80 to provide direct thermal connection or coupling between the heat sink 32 and the secondary heat sink structure 82. In that way, the metal of the secondary heat sink structure 82 may absorb the heat conducted by heat sink 32. If the reservoir portion 84 is simply solid metal or filled with a metal material, that metal would absorb heat, and thus, keep the temperature of the light-emitting device at a suitable operating point. Alternatively, if the phase change material 86 fills reservoir 84, the phase change material may melt in its absorption of heat, and thus, change phase to keep the operating point at a suitably low temperature. The circuits 66, 68 are high temperature circuits, and thus, will be suitable in their proximity to the secondary heat sink structure 82. Furthermore, a jacket of insulation 88 might surround a proportion of the secondary heat sink structure 82, such as the reservoir portion 84, and may also surround suitable electronic elements, such as the power supply circuit 28, and portions of the contacts 70 in order to protect them from the heat of the second heat sink structure 82.

Solid-liquid phase change materials absorb heat, and their temperature rises to a point where they change phase (their melting point). The materials then absorb additional amounts of heat without getting significantly hotter. When the ambient temperature in the reservoir provided by the secondary heat sink drops, the phase change material 86 solidifies, and thus, releases its stored heat. Therefore, the phase change material absorbs and emits heat while maintaining a generally constant temperature, which is desirable for the hand-held housing 12.

Another suitable phase change material is paraffin wax loaded with carbon. Once the heat sink engages with the bore hole, or channel 80 of the external heat sink, suitable thermal conduction is achieved.

The spring-loaded nature of the spring contacts 62, 64 provides a consistent and robust electrical connection between housing 12 and the tip structure 14.

Turning to FIG. 4, in accordance with another embodiment of the present invention, the power supply circuit 28 incorporates one or more ultracapacitors or super capacitors to provide the power for supplying the light-emitting device in the tip structure 14. The one or more ultracapacitors 90 could be utilized to replace batteries in the power supply circuit 28. The ultracapacitors provide high-energy storage, and are able to deliver power instantly when called upon, such as to power the light-emitting device. The ultracapacitors also charge very rapidly, sometimes in seconds, using the charging or charger circuits described herein in accordance with aspects of the invention. They can also be used to provide a necessary sudden burst of energy for applications of the device 10 of the invention. The rapid charging time provided by the power supply circuit 28 of the invention provides quick-charge applications, and eliminates the need for rechargeable batteries, which may require hours to fully charge. Furthermore, ultracapacitors have greater useful life. While a NiMH battery might be charged 500 cycles, or a Li-Ion battery 300 cycles, the present invention uses ultracapacitors that might be charged 500,000 cycles. Furthermore, such ultracapacitors that are charged and discharged as described herein do not have a memory (like battery units), have a reduced weight and cost, and do not yield hazardous waste upon disposal. For example, NiMH and Li-Ion batteries weigh significantly more on average than ultracapacitors.

A device 10, utilizing the features of the present invention, may be coupled to a suitable external power source, such as in a power base or dock 27 with sufficient contacts to engage the contacts 70 of device 10 (FIG. 1A). The ultracapacitors 90 may be charged and then discharged over a series of use cycles, such as curing cycles, for the device 10. The device may then be replaced into its charging base, or dock, to recharge the ultracapacitor. Generally, the ultracapacitor elements will not need replacement during the lifetime of the device 10, as would batteries. Since the ultracapacitors 90 charge very rapidly, the down time between charging cycles for a device 10 is very short. For example, while a NiMH battery or Li-Ion battery might take around 2.5 hours to charge fully, an ultracapacitor, as charged in accordance with the circuits of the invention, might be fully charged in 15 seconds.

FIG. 6 is a circuit schematic of one possible charging or charger circuit to be utilized within the base unit or dock 27 for charging device 10 and particularly for charging the ultracapacitors that would be provided in one such embodiment of the invention. Charger circuit 100 includes a power supply circuit/component 102 that provides suitable DC power to the circuit. For example, the power supply 102 may be coupled with an appropriate AC power cord 104 for plugging into an AC outlet, and provides DC power within the range of 5-24 Volts, for example. An indicator LED 106 might be used to provide an indication that the base 27 has power. (See FIG. 1A.) As shown in FIG. 1A, base 27 might also include indicators 111, 113 for indicating that device 10 is charging or fully charged. Circuit 100 is configured to operate as a current source in the form of a current foldback circuit, in accordance with one embodiment of the present invention. The current foldback circuit 100 is utilized to charge the ultracapacitor power supply circuit 28 of the invention, and provides a desirable rapid charge of the ultracapacitor elements 90 that differs from over how the capacitor might be charged generally. Specifically, in one embodiment of the invention, a current source is utilized to charge the ultracapacitor elements 90.

Figure 9A:
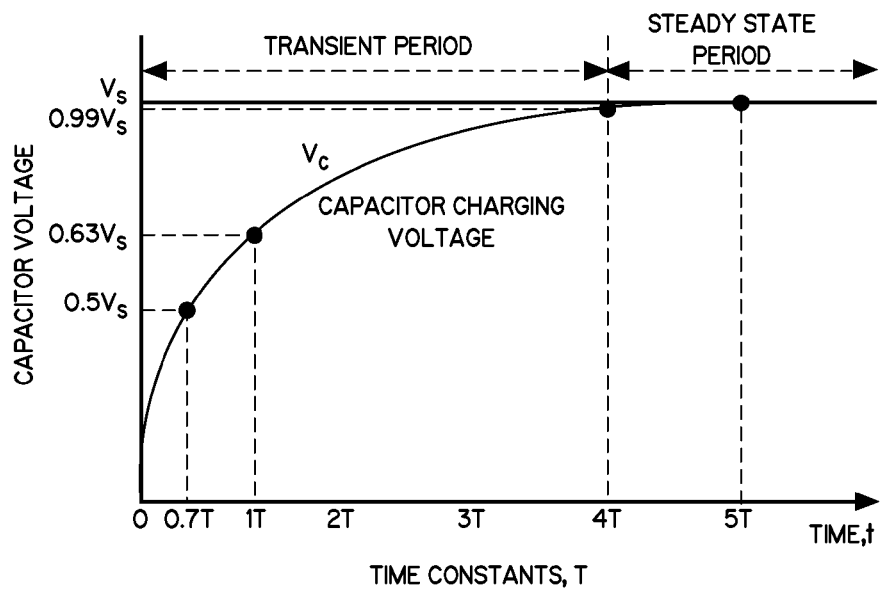
FIG. 9A is a graphical depiction of a capacitor charging curve.
Figure 9B:
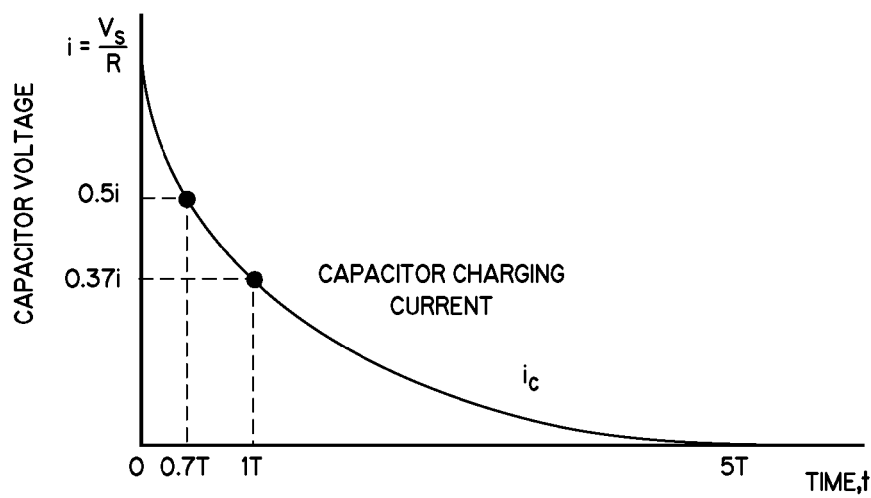
FIG. 9B is a graphical depiction of a capacitor discharging curve.

FIGS. 9A and 9B illustrate typical charge and discharge curves for a regular capacitor. For example, FIG. 9A shows a charge curve, and FIG. 9B shows a discharge curve. In general capacitor theory, the charge and discharge curves of a capacitor are considered to be exponential, as illustrated in FIGS. 9A and 9B. A single time constant, or 1T, indicates the amount of time that it takes for a capacitor to charge generally to around 63% of its full charge. The time for a full charge is expressed as 5T, as may be seen in FIG. 9A. FIG. 9B shows the discharge curve that is also exponential, wherein the time constant 1T is indicative of the time it takes to discharge to about 37% of its full charge.

However, in the present invention, it is necessary to charge ultracapacitors faster than traditional charging for the purposes of efficient use by an operator of the device 10 of the invention. That is, for certain uses, such as for curing dental compounds, it is desirable to charge the ultracapacitor very rapidly to avoid waiting and downtime in the curing process. In accordance with one embodiment of the invention as shown in FIG. 6, a current source power supply circuit 100 is used to charge the ultracapacitor at the desired rate. As illustrated in FIG. 8, the invention provides a rapid, generally non-exponential charge function for the ultracapacitor. FIG. 8 illustrates a charging ultracapacitor voltage versus time for the charger circuit of FIG. 6, and it may be seen that a very steep linear slope and charging is provided by the invention for providing a linear change function, as shown in FIG. 6. This provides significant advantages for the invention.

Returning again to FIG. 6, circuit 100 acts as a linear power supply with a current foldback function. FIG. 7 illustrates a curve associated with the operation of a current foldback supply, as illustrated in FIG. 6. When the power supply is connected to be charged, such as when device 10 is placed into the charging base 27, current is constant until the ultracapacitors are fully charged, and then there is effectively little or no output current to the ultracapacitors.

Charger circuit 100 utilizes a linear adjustable voltage regulator 108, such as an LM1084IT regulator available from National Semi-Conductor. In circuit 100, regulator 108 is a standard linear regulator where the control feedback signal is controlled by the transistor Q1 voltage Vbe. The current, through the charging ultracapacitor elements coupled to a connector 109, develops a voltage across sensing resistors (R3/R4). When the voltage across the sensing resistors is equal to the Vbe of transistor Q1 (0.6V), the transistor turns ON, and forces the linear voltage regulator 108 to foldback and limit the current generally to a value of I=0.6V/R3+R4. Once the ultracapacitors are fully charged, the current is generally or effectively 0 Amps. The capacitor charge time with such a circuit acting as a current source is illustrated in FIG. 8 as approximately T=C(V/I).

The constant power charging topology, as utilized in the invention and disclosed herein, generally transfers all the available power from the charging source or base into the energy storage ultracapacitors. The straight linear constant current or power delivery can generally provide a recharge of the power supply of the invention faster than 1T versus having to wait up to 5T, as with conventional charging of a capacitor. Effectively, the practical charge time will be set by the maximum peak current that the ultracapacitors can accept.

While FIG. 6 illustrates a charger circuit 100 that is a linear constant current foldback power supply, another alternative embodiment of the invention for fast ultracapacitor charging is to use a switched mode current mode power supply with pulse limit and pulse-by-pulse limit. In another embodiment, a lithium Ion (Li-Ion) battery charger might be utilized. Alternatively, a nickel metal hydride (NiMH) battery charger might also be utilized for the purposes of charging the ultracapacitors.

For the purposes of the invention, various different ultracapacitors might be utilized. In one embodiment, the ultracapacitor element or elements has a capacity of around 150 Farad. A range of 50-1,000 Farad might be suitable for the purposes of the invention. A multi-layer ultracapacitor might be utilized, such as one from Illinois Capacitor. Alternatively, ultracapacitors made from carbon nanotubes might also be utilized. In still another embodiment, an ultracapacitor made from carbon aerogel might be used. Lithium Ion ultracapacitors might also be utilized and provide significant cycling (e.g., 100,000 cycles) with a very low self-discharge characteristic. Another desirable feature of ultracapacitors is that they may be smaller, thinner, and lighter than conventional power supplies, such as rechargeable batteries.

Figures 13, 14:
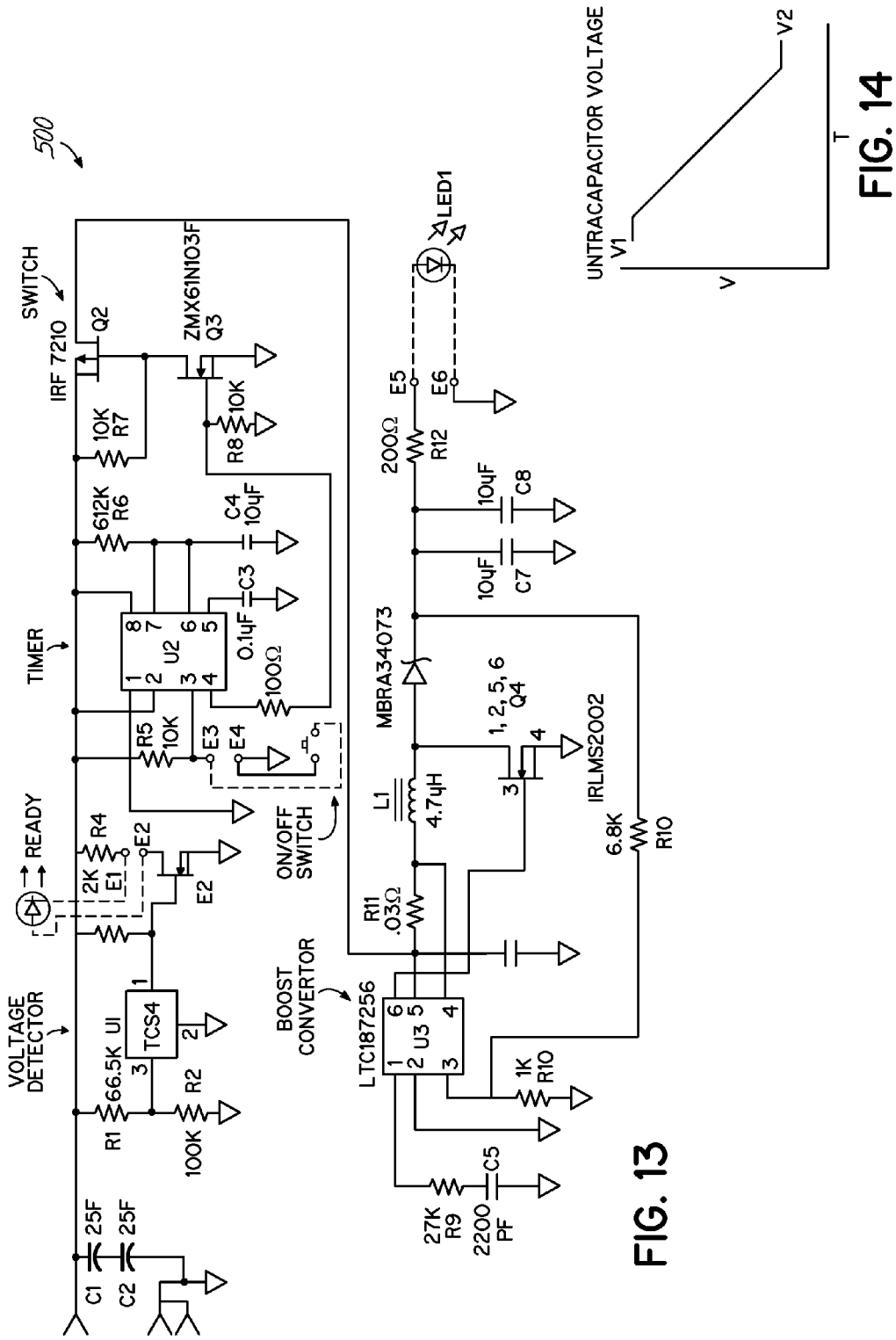
FIG. 13 is a circuit schematic showing a power supply current source circuit for another embodiment of the invention.
FIG. 14 is a graphical depiction of a discharge function according to an embodiment of the invention.

In one embodiment of the invention, the device 10 is utilized for curing dental compounds. In such an application, the LEDs that are used for the light device or engine 40 are generally high-power blue LEDs, such as an array of such LEDs. Such devices are generally current devices, and the light output from the LEDs is a direct function of the current provided from the power supply. In accordance with one aspect of the invention, to maintain a constant light output, the current to the LED elements or array 40 should be constant. In one feature of the invention, the present invention provides a current source to power the LEDs. That is, the ultracapacitors are discharged as a current source. To that end a desirable discharge function for the ultracapacitors of the invention is a straight linear function, as shown in FIG. 14, where the discharge time would be:

$$T_{discharge} = C(V1-V2)/I$$

Where V1 is the full charge voltage and V2 is the lowest operating voltage.

In one embodiment of the invention, the power supply to drive the one or more LED elements or an array making up light engine 40 could be a boost pulse width modulated (PWM) current source, or a buck PWM current source. Alternatively, a buck-boost PWM current source might be utilized. Also, a flyback current source or SEPIC current source might be used as discussed below. A buck-boost topology would provide a desirable long run time (discharge time) for device 10 by providing power to the one or more LED elements when the ultracapacitors are fully charged and the voltage may be higher than the forward voltage necessary for the LED. Such a topology then also provides power to the LED when the charge on the ultracapacitors due to discharge is lower than the forward voltage for the LED. In one embodiment, using two 100 F ultracapacitors, 30-40 discharge curing cycles of 10 second each might be achieved on a single charge, for example.

Figure 10:
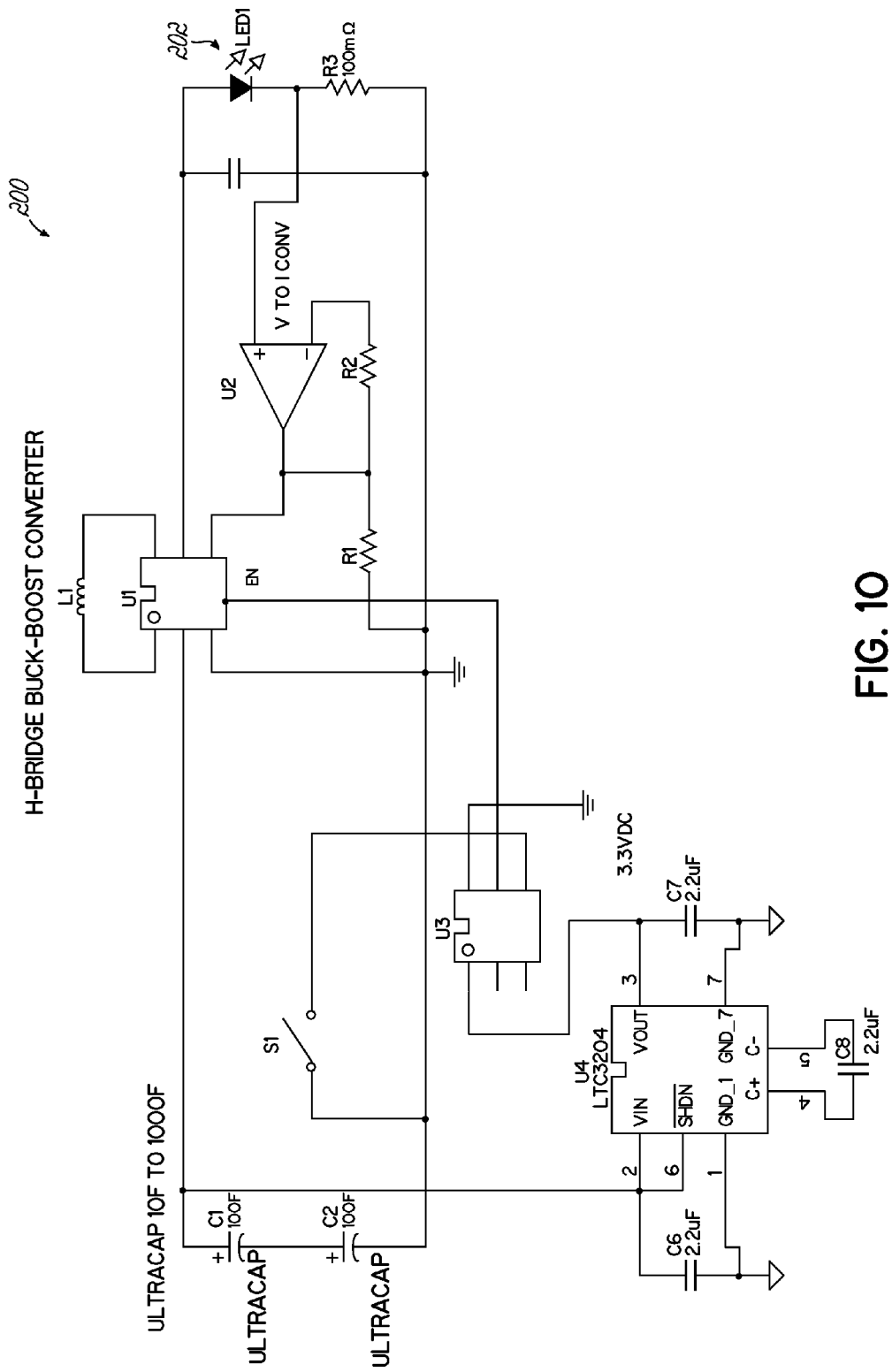
FIG. 10 is a circuit schematic showing a power supply current source circuit for one embodiment of the invention.

FIG. 10 illustrates one embodiment of a suitable buck-boost converter 200 for use in an embodiment of the invention. The embodiment illustrated in FIG. 10 illustrates two ultracapacitors C1, C2. Alternatively, a single ultracapacitor might be utilized. Still further, more than two ultracapacitors might be utilized to realize the invention, as discussed below. As such, the present invention is not limited to any particular number of ultracapacitors that might be utilized in the power supply.

Power supply circuit 200 utilizes a PWM integrated circuit U1. U1 is coupled with inductor L1 and provides power to one or more LEDs. FIG. 10 illustrates symbolically a single LED1, however, such a symbol also covers an array of multiple LEDs. PWM circuit U1 provides power through a current sensing resistor R3. The power supply might be controlled through an ON/OFF switch S1 coupled with a suitable control circuit U3, which provides ON/OFF control and timing functionality for the operation of the LEDs and the light device. Circuit U4 provides a local power supply for the U3 control circuit. In order to control U1 as a current source in the present invention, circuit U2, such as an operational amplifier, converts the current through the LED, sensed by resistor R3, into a feedback voltage. The feedback voltage is used to control the U1 circuit as a current source, as desired. Resistors R1 and R2 set the voltage feedback level to the U2 circuit.

Figure 11:
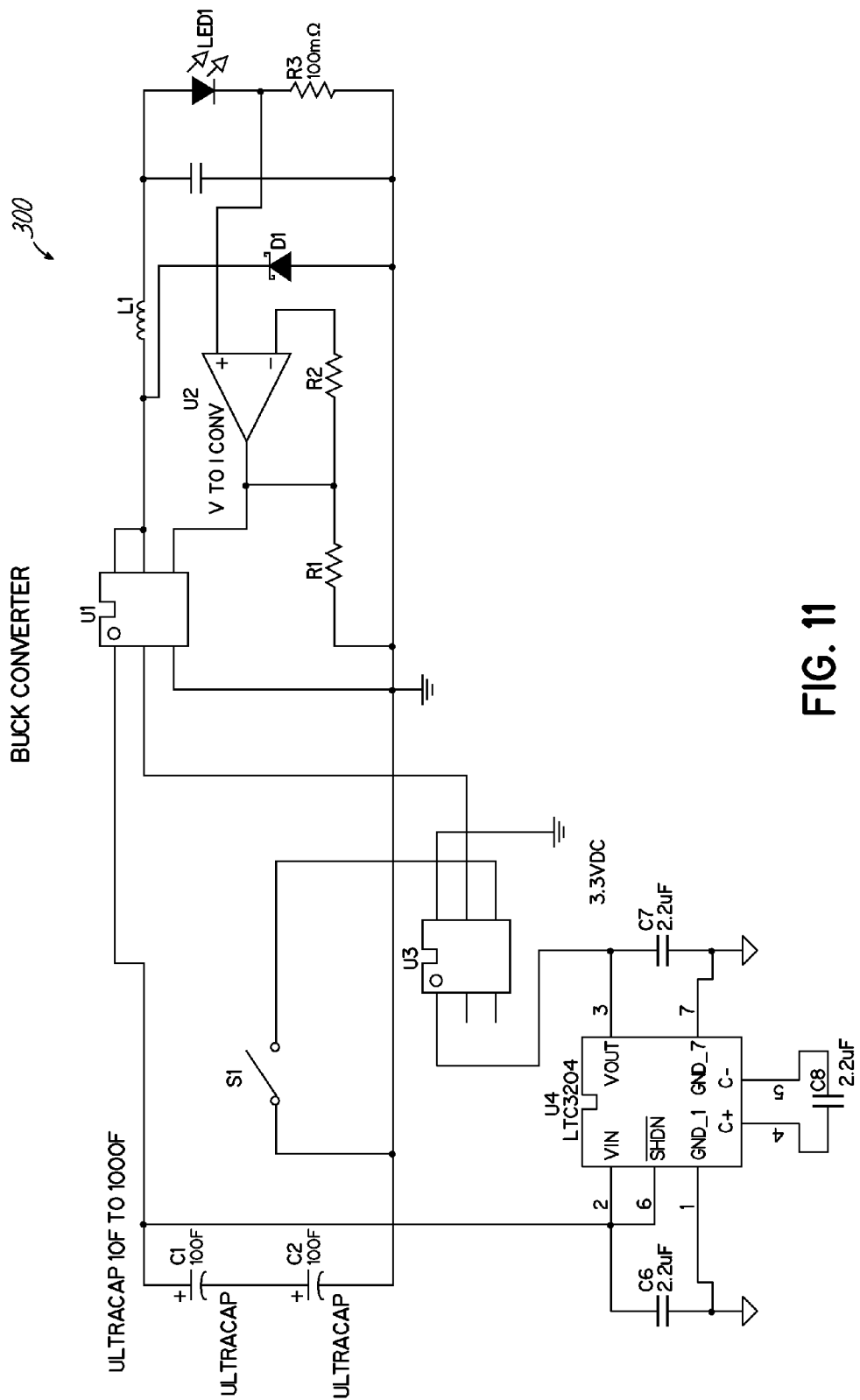
FIG. 11 is a circuit schematic showing a power supply current source circuit for another embodiment of the invention.

In an alternative embodiment of the invention, a buck converter power supply 300 might be utilized to provide a constant power load on the ultracapacitors and provide a constant current to any LED element. A buck converter topology, as illustrated in FIG. 11, somewhat resembles the buck-boost topology, as set forth in FIG. 10 with like elements sharing like reference numerals. The power path from the PWM circuit U1 includes a Schottky diode element D1 and inductor L1, as illustrated. The buck converter circuit 300 might be utilized if the LED light engine voltage requirement is less than the ultracapacitor stack voltage.

Figure 12:
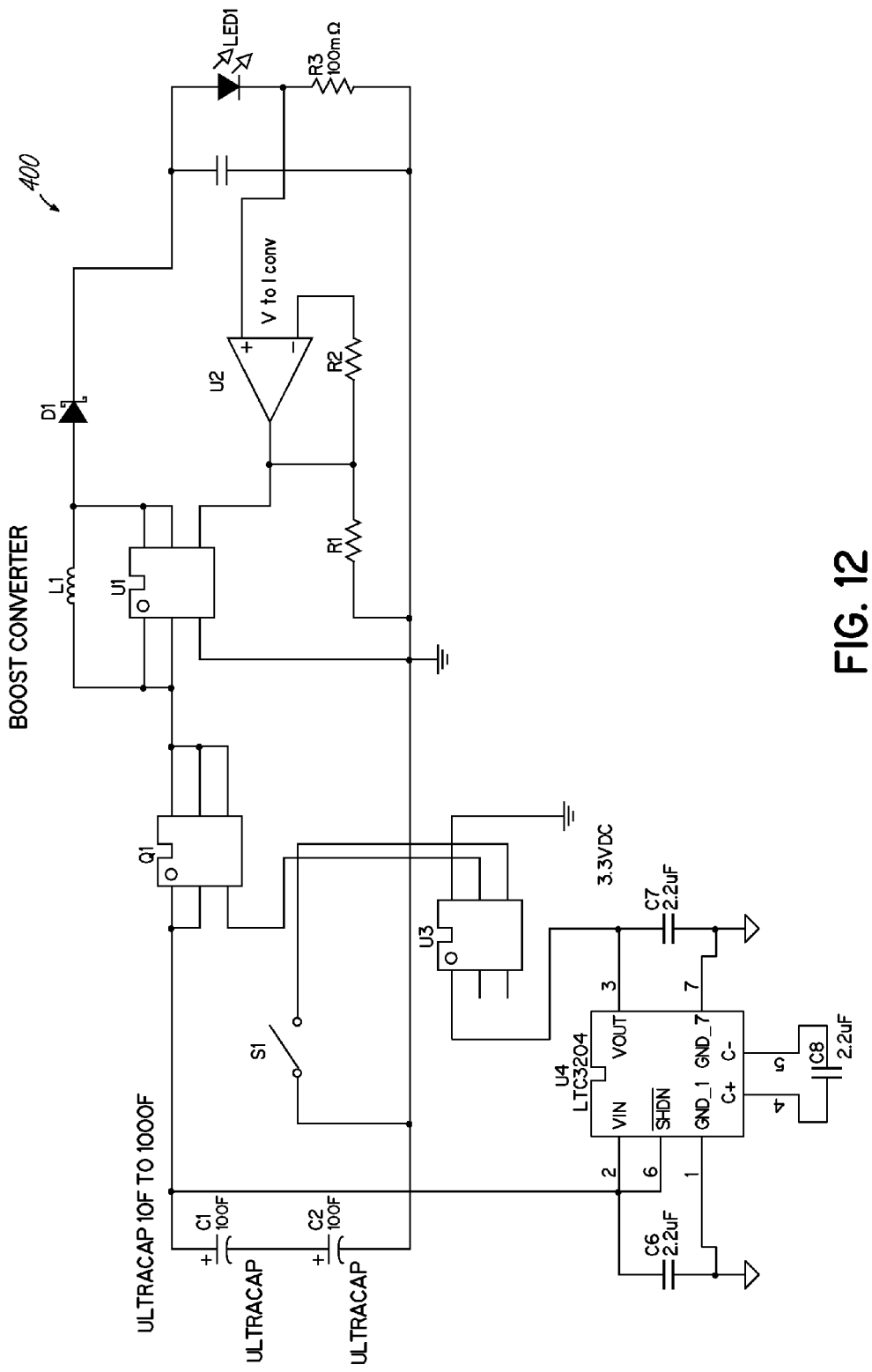
FIG. 12 is a circuit schematic showing a power supply current source circuit for another embodiment of the invention.

Alternatively, if the LED light engine voltage requirement is greater than the ultracapacitor stack voltage, a boost converter topology might be utilized. For example, the boost converter circuit 400, as illustrated in FIG. 12, might be used to drive the LED light engine. FIG. 12 resembles FIG. 10, with like reference numerals being utilized for like elements. In the boost topology of circuit 400, a solid state switch Q1 provides the functionality to turn the power supply ON/OFF based on the control of switch S1. Such a switch Q1 might also be desirable for circuits 200 and 300 as well. Schottky diode D1 and inductor element L1 are coupled appropriately for the boost converter operation.

In the circuits of FIGS. 10-12, 15, 16, PWM circuit U1 can be a standard buck, boost, or buck-boost PWM circuit that can operate at low voltages, such as from 1.5 Volts to 12 Volts. In each of the five circuits, the U2 circuit element is utilized to control the voltage feedback to the PWM U1 to provide the current source function. The voltage across the R3 element is directly proportional to the current through the LED, and the error amplifier amplifies the small voltage drop across the low Ohm sensing resister R3 to equal the internal PWM reference voltage. The U3 circuit is a control circuit that controls the ON time of the light engine and the shutdown when the ultracapacitor has discharged to a point that is too low for use by the PWM circuit U1. The U3 circuit could be a microprocessor, microcontroller, complex programmable logic device (CPLD), or a simple analog timer, such as a ZSCT1555. The U4 circuit is a charge pump power supply that acts as a low power buck-boost controller, and provides a stable, constant supply voltage to the control circuit during the discharge of the ultracapacitor. The Q1 circuit acts as a solid state switch to disconnect the LED power supply from the ultracapacitors when the power supply is turned OFF. The power circuit 400 illustrated in FIG. 12 utilizes the Q1 element. Such a solid state switch Q1 may or may not be necessary with the buck converter of FIG. 11 or the buck-boost converter of FIG. 10. Inductor element L1 is an electronic element required for the switched power mode power supply (SMPS). The value of L1 could range generally from 1 µH up to 300 µH. The D1 element, as noted above, is a Schottky diode that generally would be utilized for the buck or boost converter configurations of FIGS. 11 and 12.

Figure 15:
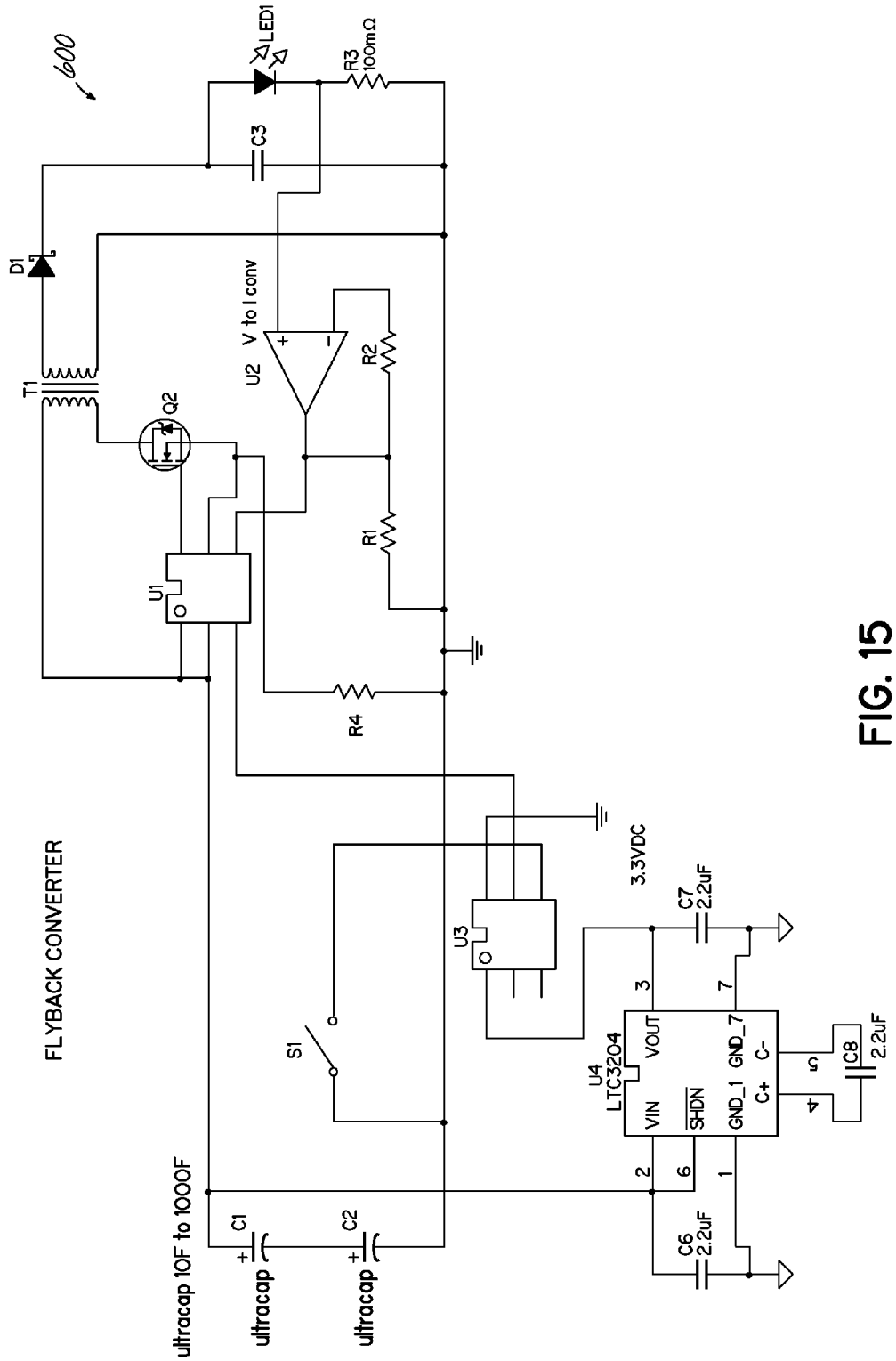
FIG. 15 is a circuit schematic showing a power supply current source circuit for another embodiment of the invention.

FIG. 15 illustrates and alternative current source for powering the LED light engine in accordance with an embodiment of the invention. FIG. 15 illustrates a flyback current source 600, wherein similar elements are used, as noted above, with respect to other embodiments. In FIG. 15, T1 indicates a flyback transformer and element Q2 illustrates a flyback switch, wherein resistor R4 is a current limit sensing resistor for switch Q2. In operation, when the switch Q2 is ON, the primary of the transformer T1 is directly connected to the input voltage source. The voltage across the secondary winding is negative, so the diode D1 is reverse-biased (i.e., blocked). The output capacitor supplies energy to the output load, such as LED 1. When the switch is OFF, the energy stored in the transformer is transferred to the output of the converter. The feedback signal from the current sensing resistor R3 is sent back to the PWM circuit U1 to control the LED current.

Figure 16:
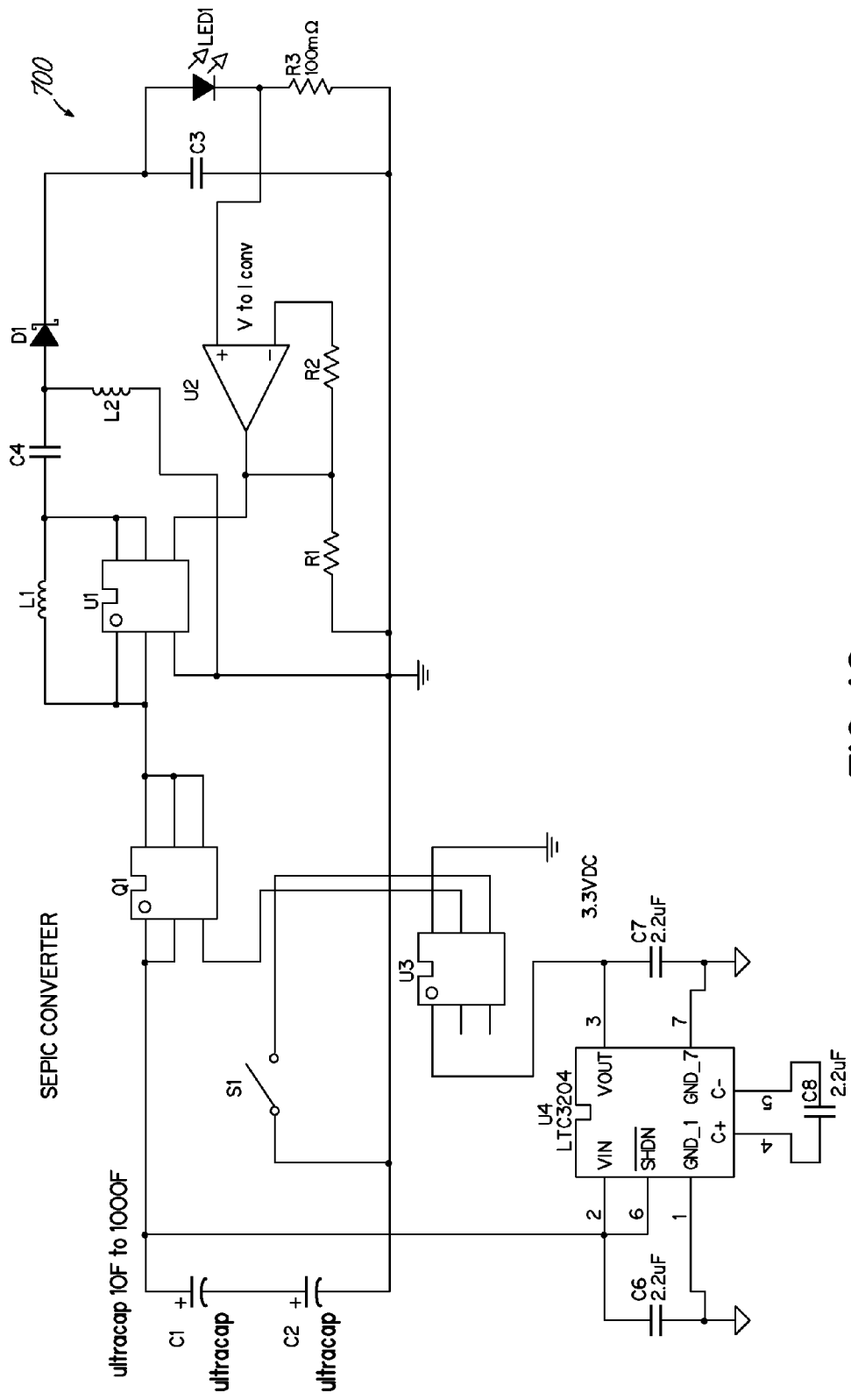
FIG. 16 is a circuit schematic showing a power supply current source circuit for another embodiment of the invention.

FIG. 16 illustrates another alternative current source in the form of a "single-ended primary inductor converter" (SEPIC) converter 700. A SEPIC converter is a type of DC-DC converter that allows the electrical voltage at its output to be greater than, less than, or equal to, that of its input. The output of the SEPIC converter is controlled by the duty cycle of the U1 circuit from the feedback signal from current sense resistor R3 that is sent back to the U1 PWM circuit to control the LED current. Similar references are used in FIG. 16 as used in FIGS. 10-13 and 15. Q1 is a solid state switch that turns the power supply ON/OFF. The split inductors L1 and L2 provide the boost function (L1) and the buck function (L2). Capacitor C4 provides AC coupling in the circuit of FIG. 16.

While the various FIGS. 10-13, 15, 16 illustrate two ultracapacitors C1 and C2 in series, a single ultracapacitor might be utilized, as noted above. Alternatively, the ultracapacitors C1, C2 might be connected together in parallel. Still further, more than two ultracapacitors might be utilized, and they might be coupled together in a series-parallel arrangement to provide the required voltage and power for the light device 10.

In an alternative embodiment of the invention, the circuit as illustrated in FIG. 13 might be utilized, such as for providing power to lower power LEDs for applications other than curing dental compounds. Circuit 500 in FIG. 13 is in the form of a boost converter, which is powered by ultracapacitors C1, C2. A voltage detector portion of the circuit provides power to a "Ready" LED (See FIG. 1A) to indicate that the light device 10 is fully charged. An ON/OFF switch portion powers a timer circuit, which drives a solid state switch Q2 to turn the power supply ON and OFF after a selected period of time (e.g., 5-40 seconds). A boost converter then provides the necessary power to an LED or LED array as shown.

While the present invention has been illustrated by the description of the embodiments thereof, and while the embodiments have been described in considerable detail, it is not the intention of the Applicant to restrict or in any way limit the scope of the appended claims to such detail. Additional advantages and modifications will readily appear to those skilled in the art. Therefore, the invention in its broader aspects is not limited to the specific details representative apparatus and method, and illustrative examples shown and described. Accordingly, departures may be made from such details without departure from the spirit or scope of Applicant's general inventive concept.

What is claimed is:

1. A curing light device for curing a compound, the curing light device comprising:
   a housing;
   a tip structure configured to be removably coupled with the housing, the tip structure having a proximal end and a distal end;
   at least one light emitting device operable for emitting light in a wavelength range suitable for curing a light curable compound, the at least one light emitting device positioned at the distal end of the tip structure;
   electrical components positioned at the proximal end of the tip structure and coupled with the at least one light emitting device, the electrical components configured for engaging complementary electrical components positioned in the housing for providing power to the at least one light emitting device;
   a portion of the tip structure extending beyond the proximal end of the tip structure, the tip structure portion configured to be received by a feature in the housing for physically aligning the tip structure in the housing and for aligning the complementary electrical components in the tip structure and housing to transfer power from the housing to the tip structure;

a power supply circuit positioned in the housing and operably coupled with the electrical components positioned in the housing, the power supply circuit being rechargeable and including at least one ultracapacitor element for being charged.

2. The curing light device of claim 1 wherein the portion of the tip structure extending beyond the proximal end of the tip structure is centrally located in the tip structure for physically aligning the tip structure in the housing.

3. The curing light device of claim 2 wherein the electrical components are positioned around the centrally located portion of the tip structure for being aligned with complementary electrical components of the housing when the tip structure is removably coupled with the housing.

4. The curing light device of claim 1 wherein the portion of the tip structure extending beyond the proximal end of the tip structure includes at least a portion of a heat sink thermally coupled with the at least one light emitting device.

5. The curing light device of claim 4 wherein the feature for receiving the tip structure portion includes a channel formed in the housing, the channel including a heat sink to thermally couple with the heat sink portion of the tip structure.

6. The curing light device of claim 1 wherein the power supply circuit includes a current source circuit coupled between the ultracapacitor element and the electrical components that is configured to discharge the at least one ultracapacitor element as a current source for driving the at least one light emitting device, the current source circuit including at least one of a buck converter circuit, a boost converter circuit, a buck-boost converter circuit, a flyback circuit and a single ended primary inductor converter (SEPIC) circuit.

7. The curing light device of claim 1 wherein the tip structure is formed of an autoclavable material capable of withstanding autoclaving.

8. The curing light device of claim 1 wherein the tip structure includes a heat sink extending from the at least one light emitting device at the proximal end to at least the distal end and insulative material covering the heat sink between the proximal end and the distal end.

9. The curing light device of claim 1 wherein the tip structure includes at least one of a transparent element or a lens for sealing the tip structure distal end proximate the at least one light emitting element.

10. The curing light device of claim 1 wherein the electrical components of at least one of the tip structure and housing are circular and can engage complementary electrical components over a range of 0° to 360°, so the tip structure may be rotated with respect to the housing.

11. The curing light device of claim 1 wherein at least one of the electrical components of the tip structure or housing includes spring contacts to ensure engagement between the complementary electrical components.

12. A curing light device for curing a compound comprising:

at least one light emitting device operable for emitting light in a wavelength range suitable for curing a light curable compound, the at least one light emitting device positioned at a distal end of the curing light device;

a heat sink system thermally coupled with the at least one light emitting device for removing heat therefrom, the heat sink system including a solid element thermally coupled with a phase change element, the solid element cooperating with the phase change element to remove heat from the at least one light emitting device.

13. The curing light device of claim 12 wherein the solid element is thermally coupled with the at least one light emitting device.

14. The curing light device of claim 12 wherein the phase change element includes a reservoir portion containing an amount of phase change material capable of absorbing heat.

15. The curing light device of claim 14 further comprising a channel coupled with the reservoir portion, the channel configured for engaging with the solid element for transferring heat from the solid element to the reservoir portion.

16. The curing light device of claim 14 wherein the phase change material includes at least one of paraffin wax or paraffin wax with carbon.

17. The curing light device of claim 12 further comprising a housing and a tip structure configured to be removably coupled with the housing, the at least one light emitting device positioned at the distal end of the tip structure, the solid element of the heat sink system being located in the tip structure.

18. The curing light device of claim 17, the phase change element being located in the housing, the solid element thermally coupling with the phase change element when the tip structure is coupled with the housing.

19. The curing light device of claim 18 further comprising a channel in the housing thermally coupled with the phase change element, the channel configured for receiving a portion of the tip structure when the tip structure is coupled with the housing.

20. The curing light device of claim 19 wherein the phase change element includes a reservoir portion containing an amount of phase change material capable of absorbing heat, the channel thermally coupled with the reservoir.

* * * * *